United States Patent
Takei et al.

[11] Patent Number: 5,992,245
[45] Date of Patent: Nov. 30, 1999

[54] PARTICLE MEASURING DEVICE FOR GRANULE PROCESSING APPARATUS AND PARTICLE MEASURING METHOD

[75] Inventors: Narimichi Takei; Kuniaki Yamanaka; Shigemi Isobe, all of Tokyo, Japan

[73] Assignees: Freund Industrial Co., Ltd., Tokyo; Shionogi & Co., Ltd., Osaka-fu, both of Japan

[21] Appl. No.: 09/051,903

[22] PCT Filed: Oct. 23, 1996

[86] PCT No.: PCT/JP96/03074

§ 371 Date: Apr. 15, 1998

§ 102(e) Date: Apr. 15, 1998

[87] PCT Pub. No.: WO97/15816

PCT Pub. Date: May 1, 1997

[30] Foreign Application Priority Data

Oct. 25, 1995 [JP] Japan ..................................... 7-276062

[51] Int. Cl.⁶ .................................................. G01N 31/00
[52] U.S. Cl. ............................................................ 73/865.5
[58] Field of Search ........................... 73/864.34, 864.35, 73/863.21, 863.23–863.25, 866, 865.5, 865.8, 863.81, 863.83, 864.81; 356/440; 348/86, 88, 92, 93

[56] References Cited

U.S. PATENT DOCUMENTS

| | | | |
|---|---|---|---|
| 2,312,295 | 2/1943 | Dahlman et al. | 73/28.05 |
| 3,475,965 | 11/1969 | Koblin et al. | 73/863.21 |
| 3,653,773 | 4/1972 | Childs . | |
| 3,760,630 | 9/1973 | Brumbaugh | 73/28.05 |
| 4,056,969 | 11/1977 | Barringer | 73/28.05 |
| 4,485,684 | 12/1984 | Weber et al. | 73/863.24 |
| 4,820,990 | 4/1989 | Moore | 73/864.35 |
| 5,058,444 | 10/1991 | Anthony et al. | 73/866 |

FOREIGN PATENT DOCUMENTS

| | | | |
|---|---|---|---|
| 2637983 | 4/1990 | France | 73/865.5 |
| 0278859 | 5/1990 | Germany | 73/865.5 |

*Primary Examiner*—Robert Raevis
*Attorney, Agent, or Firm*—McCormick, Paulding & Huber LLP

[57] ABSTRACT

In a particle measurement device 1 for a powder or granular material processing apparatus, powder or granular material is introduced into a drawing tube 3, which is formed to be projected from the inside of the granulating vessel 2, by injecting high pressure gas from the inside of the granulating vessel 2, so as to capture it with adhesive film 6. The captured powder or granular material is photographed, and, based on the obtained image information, information on the powder or granular material within the granulating vessel 2 is obtained. An air inlet 4, which is communicated with the drawing tube 3, is provided in the drawing tube 3 in the neighborhood of its end portion 3b on the side of the outside of the granulating vessel 2. Through this air inlet 4, gas having higher pressure than the inside of the granulating vessel 2 is introduced into the drawing tube 3. By this, in the particle measurement device for the powder or granular processing apparatus, effects of remaining powder or granular material and flow out of the powder or granular material are removed, and grain size etc. are measured with high reliability.

20 Claims, 11 Drawing Sheets

PARTICLE MEASURING DEVICE FOR GRANULE PROCESSING APPARATUS AND PARTICLE MEASURING METHOD

TECHNICAL FIELD

The present invention relates to a particle measurement device for a powder or granular material processing apparatus, and in particular, to techniques effectively applicable to a grain size measurement device which actually and continuously measures grain sizes, shapes, and the like of powder or granular material produced by various powder or granular material processing apparatuses such as a fluidized bed granulator apparatus, an agitation granulator, a centrifugal tumbling granulating/coating apparatus.

BACKGROUND ART

There are various processings of powder or granular material, including granulating, drying, coating, and the like. Among them, as the granulating method of powder or granular material, can be listed the fluidized bed granulating method, agitation granulating method, centrifugal tumbling granulating method, and combinations thereof or combined-type granulating methods, and they are widely employed in various fields such as pharmaceutical preparations and food.

At first, among these granulating methods, the fluidized bed granulating method comprises sprinkling liquid material on powder or granular material, which has been in a fluidized state by dispersion and mixing within a processing vessel, increasing the grain sizes gradually. As a fluidized bed granulating apparatus for such processing, may be mentioned Flow Coater (trade name) by Freund Industrial Co., Ltd. which fundamentally comprises a processing vessel for containing and processing material to be processed, a fluidizing air supply device for supplying fluidizing air so as to fluidize the material, and a spray nozzle for spraying liquid on the material. By the fluidizing air, the material to be processed comes to be fluidized, and on this fluidized material, the liquid is sprayed by the spray nozzle, to carry out the granulation.

Next, the agitation granulating method comprises dispersing and mixing solid/liquid to produce particles, by agitation with an agitating blade (agitator). As an agitation granulating apparatus for such processing, be mentioned a high speed mixer FS-G model (trade name) of Fukae Kogyo Ltd., which is called, in another name, as a high speed mixing machine. As disclosed in Japanese Patent Publication No. 6-22667, Japanese Patent Publication No. 6-24619, Japanese Un-examined Patent Laid-Open No. 5-236, and Japanese Patent Publication No. 2-32932, this agitating granulating apparatus fundamentally comprises an agitating blade rotatably provided within a processing vessel, with a bottom portion of the processing vessel serving as a fixed wall. In addition to this construction, a disintegrating blade (chopper) may be provided if necessary, as shown in Japanese Un-examined Patent Laid-Open No. 5-115766, so that disintegration granulation may be performed by the chopper, in addition to tumbling granulation by the agitator. Further, if a drying process is needed, a vacuum drying system may be provided, or otherwise, a heater may be provided on the outer periphery of the processing vessel in a jacketing manner. Then, by suitably controlling rotational speed of the agitator and the chopper, quantity of the liquid, quantity of charging, granulation time, temperature, and the like, mixing granulation of the powder or granular material is carried out.

On the other hand, the centrifugal tumbling method comprises tumbling mixing of powder material on a rotating disk, while spraying liquid on the material to make powder particles adhere to and agglomerate with one another. As a centrifugal tumbling granulating apparatus for such processing, be mentioned CF Granulator (trade name) made by Freund Industrial Co., Ltd., an automatic coating apparatus described in Japanese Patent Publication No. 54-992, and a granulating apparatus of Japanese Un-examined Patent Laid-Open No. 6-262054 (corresponding to U.S. Pat. No. 5,507, 871), and each of these apparatus fundamentally comprises a rotating disk, which rotates generally horizontally, provided at a bottom portion of a processing vessel. If necessary, slit air is supplied into the inside of the processing vessel through a ring-shaped gap formed between circumference of the rotating disk and a inside wall portion of the processing vessel, while dispersing powder and spraying liquid on the material to be processed within the processing vessel, so as to perform granulation of the powder or granular material.

Further, there has been used the combined-type granulating method which combines the above-described techniques. For example, there has been appeared an apparatus, such as Spir-A-Flow (trade name) made by Freund Industrial Co., Ltd., which fundamentally performs the fluidized bed granulation, and suitably combines it with the agitation granulation and the centrifugal tumbling granulation, using combination of a rotor disk and an agitator.

In such process of granulating powder or granular material, from the viewpoint of the object of producing particles and from the viewpoint of process validation for a product, measurement and control of particle diameter are so important as to be incomparable with the other factors. By this reason, various granulating apparatuses use a moisture meter, a pressure gauge, an electric power meter, and the like as sensors for process validation. Using these sensors, an end of granulation, granulating conditions, and the like are controlled. Here, "process validation" is defined as "a documented program giving a high-level assurance that a certain process constantly produces products compliant with preset standard and quality characteristics", and is important from the viewpoint of GMP (Good Manufacturing Practice).

However, measurement using these sensors gives only indirect "estimation" of particle diameters, and has disadvantage that error becomes large. Further, according to a granulation method, the above-described sensors may not be used. For example, in non-water type granulation using ethanol, the moisture meter can not be used. Further, each granulating method has following specific difficulty.

First, in the fluidized bed granulating method, process control generally uses an infrared absorption moisture meter such as Moiswatch (trade name) made by Okawaraseisakusho. Such a moisture meter, however, has disadvantages in that data is blurred in high moisture content area, and that variation of moisture content is smaller in comparison with variation of particle diameter. Further, in the case of granulation with constant moisture content, the end point of granulation can not be decided by such a moisture meter.

Next, in the case of the agitation granulating method, although there exist examples of validation using a pressure gauge or a resistance meter or based on power consumption, granulation is generally controlled by charge amount of raw material, added amount of binder, rotation speed of the agitating blade, and agitating time. For example, in the case of the control by power consumption, power consumption rapidly increases at the start of the granulation, repeats fluctuations as the granulation proceeds, decreases gradually as resistance to agitation decreases, and becomes steady state as the regulation of particles proceeds, and, following these stages, the end point of the granulation is decided. However, synthetic process or storage conditions of the raw material etc. may affect them so that the raw material etc. are varied in their hygroscopic property (wettability), fluidity, and powder property (characteristics of bulk) such as agglomeration or adhesion property etc. Accordingly, for validation, it is desirable to control by feedback. Further, as in the case of the control by power consumption, when granulation is made to proceed until change of load on a granulating apparatus becomes obvious, detection by a sensor is easy, but granulation tends to proceed excessively. In particular, in the case of granulation for tabletting, the excessive granulation makes the particles too hard, or produces too small amount of fine powder.

Further, in the centrifugal tumbling granulating method, an operator decides the end point of the granulation by directly feeling water content in the powder material with his hand, or by observing sampled products with a magnifying lens, for example. Judgment, however, by the operator's feeling or eye observation can not be said as objective judgment at all, and validation is impossible. On the other hand, although introduction of a moisture meter or a lever resistance type pressure gauge has been studied, a satisfactory result has not been obtained since, for example, measurement error becomes large due to adherence of the powder material to an employed sensor such as a moisture meter. In particular, in the case of an electrode-type moisture meter, powder adheres to surface of an electrode of the moisture meter, and the measurement becomes impossible in short time. In addition, a moisture meter or the like has been used mainly for maintaining of an equilibrium state of granulation process, and can not be used for deciding an end point of granulation.

Thus, there are various disadvantages for control of granulation process in respective granulating methods. In particular, the fluidized bed granulating method has a disadvantage in that variation in grain size and particle shape (referred to as "grain size etc." in abbreviation) of products is large, and various grain size control methods have been tried for this granulating method.

In that case, to make the grain size etc. of powder or granular material uniform, it is necessary to monitor the grain size etc. always in real time for change of processing conditions at any time, and to suitably decide an end point of processing for obtaining products with desired properties. For that purpose, as described above, such techniques as time management by timer control, observation by a skilled worker, control by water content value, and the like have been employed. However, the timer control or the observation by a skilled worker has a problem in accuracy. Namely, the timer control can not cope with change in bulk characteristics, and variation in product grain size can not be avoided. Further, accuracy is lacked in workings depending on skilled worker's experience or perception such as judgment of the processing state by observing the inside of a processing apparatus through its inspection hole. Further, it is difficult to give exact judgment by the control based on water content value, since change of water content does not quickly respond to rapid advance of granulation in the stage approaching the end point of the granulation. Accordingly, in many conventional cases, end of granulation is decided by judgment of grain size etc. by eye observation or measurement of granulated objects sampled in the course of the granulation process. For example, the end point is predicted by sieving the sampled products with 16 mesh sieve for 10 seconds, and by calculating based on the ratio of the particles remaining on the sieve.

Such a method, however, can not obtain data in real time, is inferior in accuracy and rapidity, and, thus, is unfavorable from the viewpoint of validity. Accordingly, to grasp, in real time, grain size etc. simply and accurately, such grain size measurement devices have been proposed as described in Japanese Un-examined Patent Laid-Open No. 4-265142, Japanese Un-examined Patent No. 7-794, Japanese Un-examined Patent Laid-Open No. 7-120374, and Japanese Un-examined Patent Laid-Open No. 8-131810.

Here, in the grain size measurement device of 4-265142, a processing vessel (granulating vessel) is provided with a drawing tube for powder or granular material, and high pressure gas is blown from the inside of the processing vessel to introduce the powder or granular material within the processing vessel into the drawing tube. Thus-introduced powder or granular material is captured by adhesive film provided in an inner part of the drawing tube, and an image of the captured powder or granular material is picked up to measure its grain size etc. After the measurement of the grain size, the inside of the drawing tube for powder or granular material is cleaned by negative pressure in the processing vessel. On the other hand, in the device of 7-794, a camera device and a high speed stroboscopic device are provided being directed toward the inside of the processing vessel, and, using these devices, a static image is obtained to measure grain size etc.

Further, as for the camera devices for granulation, coating, or the like in 7-120374 and 8-131810, camera system devices and lighting system devices are arranged within the processing vessel, and powder or granular material is made to be in a separated state by air and, then, is photographed. In that case, in the camera device of 7-120374, front end portions of the camera system and the lighting system are provided adjacently within the processing vessel, and air is supplied in the direction of photographing and in the direction at right angles with the former to put the powder or granular material in the separated state. On the other hand, in 8-131810, lighting and air injection are given obliquely in front of a lens tube containing the camera system, thus putting the powder or granular material in dispersed condition to take a picture.

Although these devices, in particular the grain size measurement device of 4-265142, are superior ones which can measure grain size etc. in real time simply and accurately, when the inside of the processing vessel is not at negative pressure, sometimes a great amount of powder or granular material adheres to the adhesive film so that it becomes impossible to measure. Further, the powder or granular material introduced in the last time remains within the drawing tube, and adheres to the adhesive film together with the powder or granular material introduced in the next time so that accurate sample can not be obtained.

Further, at the time of measurement, the adhesive film for capturing the powder or granular material is tightly fixed to the drawing tube. For next measurement, however, it should be once separated from the drawing tube and wound, so that unused portion of the film is moved to the suitable position. Thus, at the time of the movement of the film, there exist gaps between the adhesive film and the drawing tube for powder or granular material, and the powder or granular material flows out through these gaps, contaminating adjacent portions of the device and an unused portion of the adhesive film. In that case, the flowed-out powder or granular material is scattered onto the image pick-up means for obtaining sampling images, having an adverse effect on subsequent pick-ups and measurements, or making measurement itself impossible, and settlement of these problems has been desired.

On the other hand, the devices of 7-120374 and 8-131810 photograph particles by dispersing them with purging air. Thus, in an apparatus where particles are floated such as the fluidized bed apparatus, it is possible to disperse the particle, and the device of 7-120374 or 8-131810 can be used without problem for photographing particles. However, in the agitation granulating apparatus and the centrifugal tumbling granulating apparatus, a great amount of particles are in a concentrated state, and it is difficult to disperse the particles to identify an individual, and the device of 7-120374 or 8-131810 can not be applied to such a kind of granulating apparatus.

An object of the present invention is to provide a particle measurement device which can perform real-time and highly-reliable measurement of grain size etc. in various granulating apparatuses.

The above-described and other objects and new features of the present invention will be obvious from the following description and the attached drawings.

DISCLOSURE OF THE INVENTION

The inventor of the present invention has studied the cause of the above-described problems to find that the number of powder or granular material captured by adhesive film is largely affected by air pressure inside a processing vessel. Namely, owing to pressure fluctuation inside the processing vessel, occasional adhesion of a great amount of powder or granular material to the adhesive film arises since a drawing tube for powder or granular material is not cleaned sufficiently by negative pressure inside the processing vessel, and since the powder or granular material intrudes into the drawing tube at other times than the measurement time.

The particle measurement device of the present invention can be utilized in various apparatuses which perform general processing of powder or granular material such as granulating, drying, coating, or the like, including a fluidized bed granulating apparatus, a fluidized bed coating apparatus, a fluidized bed drying apparatus, an agitation granulating apparatus, a centrifugal tumbling granulating apparatus, a centrifugal tumbling coating apparatus, other combined-type granulating apparatuses, a powder or granular material extrusion granulating apparatus, a crusher, a powder or granular material recovery apparatus, and a particle regulating apparatus. Among such various apparatus for processing powder or granular material, in the apparatus utilizing the fluidized bed, such as the fluidized bed granulating apparatus, the fluidized bed coating apparatus, the fluidized bed drying apparatus, and the like, fluidizing air flow is generated by an exhaust blower, and accordingly the inside of the processing vessel is negative pressure in comparison with the outside air. Further, the end portion of the drawing tube for powder or granular material is sealed by adhesive film except for winding time. Thus, it has been considered that the powder or granular material does not flow into the inside of the drawing tube for powder or granular material except that the powder or granular material is introduced into the drawing tube by gas injection from the inside of the processing vessel. Further, it has been considered that the powder or granular material remaining within the drawing tube is sucked back by the negative pressure of the processing vessel when the seal by the adhesive film is released.

However, studies by the present inventor have revealed facts that the air pressure inside the processing vessel is not constant, but fluctuates in a wider range; that, owing to this pressure fluctuation, the powder or granular material flows into the drawing tube at other times than the measurement times, and cleaning is insufficient at times; and that, owing to these factors, the number of the captured powder or granular material is varied at measurement times. Thus, to prevent such flowing-into of the powder or granular material, and to remove the effect of the powder or granular material remaining in the drawing tube, the present inventor has completed the present invention.

Out of the inventions disclosed here, outlines of representative ones will be briefly described as follows.

Namely, a particle measurement device for a powder or granular material processing apparatus, according to the present invention, has a drawing tube for drawing out powder or granular material, provided in a granulating vessel, in such a manner that one end portion of the drawing tube is arranged in the inside of the processing vessel, and that the other end portion is communicated with said one end portion and positioned in the outside of the processing vessel. Further, the present device comprises a gas injection nozzle for injecting high pressure gas from the inside of the processing vessel into the drawing tube, so as to introduce the powder or granular material within the processing vessel into the drawing tube. Further, the device comprises an adhesive film which has an adhesive surface arranged opposed to an opening of an end surface of the drawing tube on the side of the outside of the processing vessel, so as to capture, with said adhesive surface, the powder or granular material which has passed the drawing tube; an image pick-up means for photographing the powder or granular material captured by the adhesive surface of the adhesive film; and an information processing means for processing image information of the powder or granular material obtained by the image pick-up means. The device is characterized in that, in the neighborhood of the end portion of the drawing tube on the side of the outside of the processing vessel, is provided an air inlet communicated with the drawing tube, and gas having higher pressure than the inside of the processing vessel is introduced into the drawing tube through the air inlet.

Further, in order to remove effects by powder or granular material flowing out from the drawing tube, in the particle measurement device for a powder or granular material processing apparatus, such as described above, comprising a drawing tube, a gas injection nozzle, an adhesive film, an image pick-up means, and an information processing means, the adhesive film and the end portion of the drawing tube opposed to the adhesive film may be housed within a box having an air feed port, so as to introduce gas, which has higher pressure than the inside of the processing vessel, into the box through the air feed port. In that case, an air communicating port communicated with the drawing tube may be provided in the neighborhood of the end portion of the drawing tube, in such a manner that this air communicating port is housed within the box together with the adhesive film and the end portion of the drawing tube opposed to the adhesive film.

By this construction, in the particle measurement device which employs such a method of measuring grain size etc. of the powder or granular material that the powder or granular material is introduced into the drawing tube, captured by the adhesive film, and photographed, effects of the powder or granular material remaining in the drawing tube and the powder or granular material flowing out from the tube can be eliminated.

The above-described powder or granular material processing apparatus may be a fluidized bed granulating apparatus or a fluidized bed coating apparatus, a fluidized bed drying apparatus, an agitation granulating apparatus, a centrifugal tumbling granulating apparatus, or a centrifugal tumbling coating apparatus. In that case, of course, the particle measurement device according to the present invention can be applied to a powder or granular processing apparatus other than the above-described granulating apparatuses, the coating apparatuses, and the drying apparatus, namely, to such processing apparatuses as, for example, a powder or granular material extrusion granulating apparatus, a crusher, a powder or granular material recovery apparatus, a powder or granular material regulating apparatus and the like.

Further, the above-described particle measurement device may be installed downstream from the powder or granular material processing apparatus which can perform continuous processing of the powder or granular material, so as to control processing conditions of the above-described powder or granular material processing apparatus based on a result of the measurement by the particle measurement device. In that case, the particle measurement device may be installed in a powder or granular material transport pipe arranged between powder or granular material processing apparatuses.

On the other hand, a method of particle measurement for a powder or granular material processing apparatus, according to the present invention, is one which uses the above-described particle measurement device provided with the air inlet, and in that method, high pressure gas is injected from the gas injection nozzle so as to introduce powder or granular material inside the processing vessel into the drawing tube; the powder or granular material which has passed the drawing tube is captured by the adhesive surface of the adhesive film; and the powder or granular material captured by the adhesive film is photographed to obtain image information, and, based on the obtained image information, information on the powder or granular material within the processing vessel is obtained. In that method, the particle measurement is performed while gas having higher pressure than the inside of the processing vessel is always introduced into the drawing tube through the air inlet. In that case, the measurement is performed in such a state that the powder or granular material remaining in the drawing tube is returned into the processing vessel by the introduced gas, and the powder or granular material does not enter into the drawing tube from the side of the processing vessel except for measurement time.

Further, the present invention provides a method of particle measurement, using the above-described particle measurement device in which the adhesive film and the end portion of the drawing tube opposed to the adhesive film are housed in the box having the air feed port, and in that method, the particle measurement is performed while the adhesive film is tightly fixed to an end surface of the drawing tube, and the adhesive film is separated from the end surface and exchanged for an unused adhesive film, at every end of the measurement. And, by introducing the gas having the higher pressure than the inside of the processing vessel into the box through the air feed port at least when there is a gap between the adhesive film and the drawing tube, the inside of the box is kept at higher pressure than the inside of the processing vessel.

Further, the present invention provides a method of particle measurement, using the particle measurement device which is provided with an air communicating port also housed in the above-described box, and in this method, the particle measurement is performed while the gas having the higher pressure than the inside of the processing vessel is always introduced into the box through the air feed port so as to keep the inside of the box at higher pressure than the inside of the processing vessel.

The above-described powder or granular material processing apparatus may be a fluidized bed granulating apparatus or a fluidized bed coating apparatus, a fluidized bed drying apparatus, an agitation granulating apparatus, a centrifugal tumbling granulating apparatus, or a centrifugal tumbling coating apparatus. In this case too, of course, the particle measurement device according to the present invention can be applied to a powder or granular processing apparatus other than the above-described granulating apparatuses, the coating apparatuses, and the drying apparatus, namely, to such processing apparatuses as, for example, a powder or granular material extrusion granulating apparatus, a crusher, a powder or granular material recovery apparatus, a powder or granular material regulating apparatus and the like.

Further, the present invention provides a method of controlling a powder or granular material processing apparatus, characterized in that the above-described particle measurement device is installed downstream from a powder or granular material processing apparatus which can perform continuous processing of the powder or granular material, and processing conditions of the powder or granular material processing apparatus are controlled based on a result of the measurement by the particle measurement device. In that case, the particle measurement device may be installed in a powder or granular material transport pipe arranged between the powder or granular material processing apparatuses.

Further, a program for making a computer execute the above-described method according to the present invention may be stored and handled in a medium.

BEST MODE FOR CARRYING OUT THE INVENTION

Figure 1:
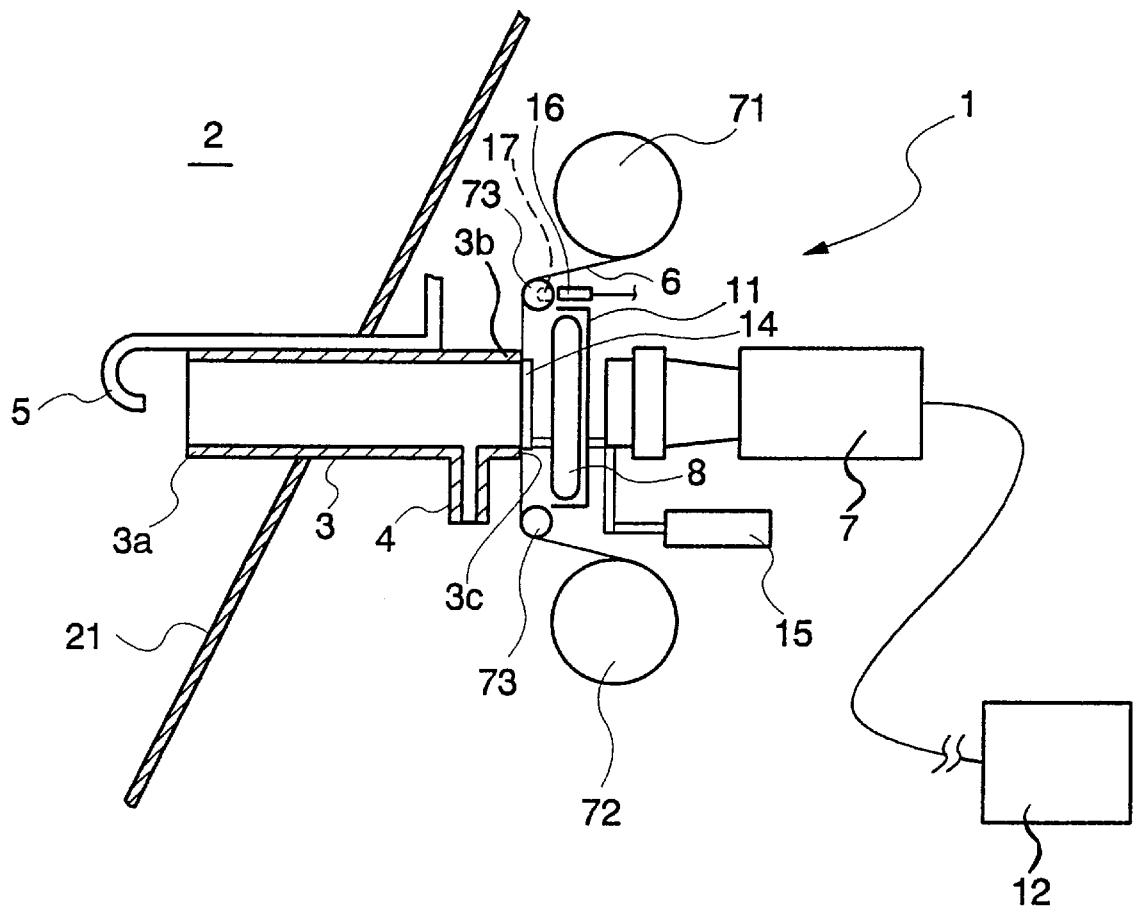
FIG. 1 is a partially sectional plan view showing construction of a particle measurement device for a powder or granular material processing apparatus, as a first embodiment of the present invention.

Now, embodiments of the present invention will be described in detail referring to the drawings.

Figure 2:
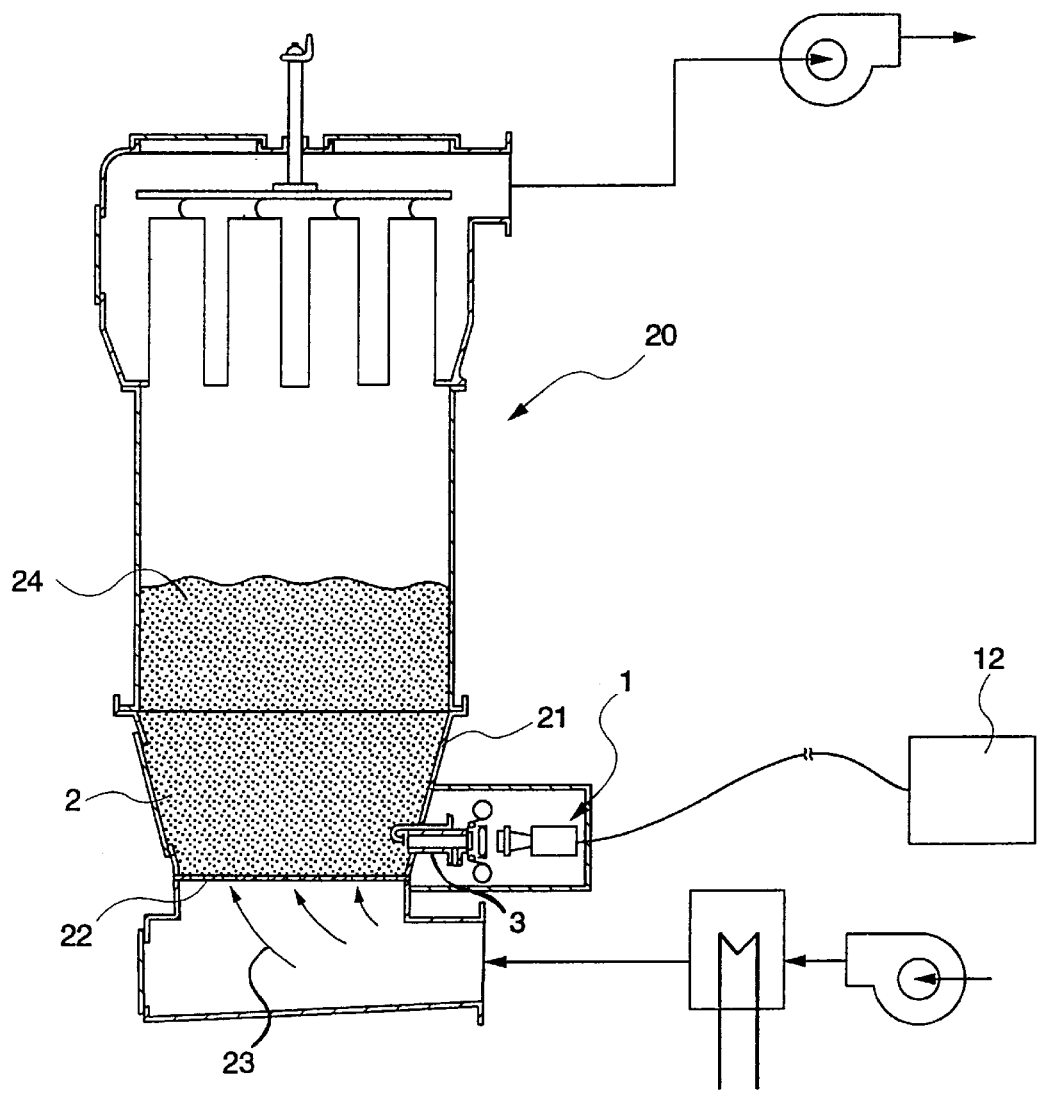
FIG. 2 is an explanatory view showing a state where the particle measurement device of FIG. 1 is attached to the powder or granular material processing apparatus.

FIG. 1 is a plan view showing construction of a particle measurement device for a powder or granular material processing apparatus, as Embodiment 1 of the present invention; and FIG. 2 is an explanatory view showing a state in which the particle measurement device of FIG. 1 is attached to the powder or granular material processing apparatus. In this FIG. 1, a part of the construction is shown in section. In this Embodiment 1, the powder or granular material processing apparatus is assumed to be a fluidized bed granulating apparatus. Further, a drawing tube 3 of the particle measurement device 1 for drawing the powder or granular material is provided with an air inlet 4 for cleaning the inside of the tube. By introducing clean gas through this air inlet 4, the powder or granular material remaining within the drawing tube 3 is returned into the inside of a granulating vessel (processing vessel) 2 so that the inside of the drawing tube 3 is cleaned and, at the same time, intrusion of the powder or granular material from the granulating vessel 2 into the drawing tube is prevented.

First, construction of the particle measurement device 1 in Embodiment 1 will be described. This particle measurement device 1 measures grain size etc. of the powder or granular material being fluidized within the granulating vessel 2 of the fluidized bed granulating apparatus (powder or granular material processing apparatus) 20. As shown in FIGS. 1 and 2, the particle measurement device 1 is mounted onto a side wall 21 of the granulating vessel 2 having an inverted cone shape with an upper portion being of larger diameter. The mounting location of the device is not limited to the surface of the side wall 21, though it is preferable that the particle measurement device 1 is mounted at a place where grain density is high.

Here, the powder or granular material fluidized within the granulating vessel 2 is affected by air classification, and grain size distribution varies with the location within the fluidized bed. The powder or granular material in a lower portion of the fluidized bed shows a distribution generally similar to population, while, in a upper portion of the fluidized bed, a distribution is one including more fine particles. Accordingly, it is preferable that measurement of grain size etc. aims at the powder or granular material existing in the lower portion of the fluidized bed. To that end, as shown in FIG. 2, the particle measurement device 1 in question is mounted on a relatively lower portion of the granulating vessel 2. Of course, the mounting location is not limited to the one shown in FIG. 2.

The particle measurement device 1 is so provided with the drawing tube 3 of a cylindrical shape that the drawing tube is projected from the inside of the granulating vessel 2 to the outside. An end portion 3a of the drawing tube 3 is opened toward the inside of the granulating vessel 2 so that the drawing tube 3 is communicated with the inside of the granulating vessel 2.

Further, the fluidized bed granulating apparatus 20 is common one in which fluidizing air 23 is introduced into the fluidized bed granulating apparatus 20 from an under side of a perforated plate 22 provided in a bottom portion of the apparatus 20, and, by this, the powder or granular material 24 is fluidized and granulated within the granulating vessel 2. Of course, the particle measurement device 1 in question can be applied to various fluidized bed granulating apparatus such as one disclosed in Japanese Un-examined Patent Laid-Open No. 6-319978, for example.

In Embodiment 1, the air inlet 4 is provided in the neighborhood of an end portion 3b located in the drawing tube 3 on the side of the outside of the granulating vessel 2. This air inlet 4 is communicated with the drawing tube 3, and gas introduced through the air inlet 4 passes the drawing tube 3 to flow into the granulating vessel 2. In Embodiment 1, clean gas is introduced through the air inlet 4 into the drawing tube 3. By this clean gas, the powder or granular material remaining in the inside of the drawing tube 3 is returned into the inside of the granulating vessel 2 so that the inside of the drawing tube 3 is cleaned.

In the neighborhood of the end portion 3a of the drawing tube 3, a gas injection nozzle 5 is mounted. The gas injection nozzle 5 is so crudely arranged that a tip of the nozzle 5 is opposed to an opening of the end portion 3a of the drawing tube 3. High pressure gas is supplied from a gas supply means not shown, and the high pressure gas is injected instantaneously from the tip toward the drawing tube 3. By this injection, the powder or granular material in the granulating vessel 2 is introduced into the drawing tube 3, and scattered toward the end portion 3b.

On the other hand, the end portion 3b on the side of the outside of the drawing tube 3 is opened toward the outside of the granulating vessel 2, and adhesive film 6 is arranged to be opposed to an end surface 3c of the end portion 3b. The adhesive film 6 is formed of transparent resin tape coated with also transparent adhesive material on one surface of the tape, and is placed so that the adhesive surface is opposed to the end surface 3c. Namely, the powder or granular material introduced into the drawing tube 3 by the injection from the gas injection nozzle 5, is captured by the adhesive tape 6 in this area.

The adhesive film 6 is one wound in a roll shape, supported by a roll supporting portion 71, and intermittently drawn out by given length in accordance with measurement of the powder or granular material. After moving along the end surface 3c of the drawing tube 3 through guide rollers 73, 73, the adhesive film 6 is wound by a motor reel 72. At that time, the adhesive film 6 is tightly fixed to the end surface 3c when the powder or granular material is measured, and, after the end of the measurement, is peeled from the end surface 3c, and is wound in preparation for the next measurement. Then, an unused portion of the adhesive film 6 is moved to the position opposed to the end surface 3c, and is tightly fixed to the end surface 3c again.

For tightly fixing the adhesive film 6, there may be employed various methods such as one that a transparent or frame-shaped push plate or the like is pushed against the adhesive film 6 at the back of the film 6, or a method utilizing the tensile force of the adhesive film 6. In Embodiment 1, this is done by driving a film keep plate 14 with an air cylinder 15. Namely, the air cylinder 15 pushes the film keep plate 14 against the back of the adhesive film 6, so that the adhesive film 6 is pushed against the end surface 3c of the drawing tube 3 so as to be tightly contacted with the end surface 3c. As a result, the drawing tube 3 is kept in a sealed state by the adhesive film 6 except when the adhesive film 6 is wound.

For adjusting winding length of the adhesive film, the particle measurement device 1 of Embodiment 1 in question is provided with a sensor 16 for detecting movement of the guide roller 73. This sensor 16 comprises a proximity switch, and detects passing of a hole 17 formed in the guide roller 73. Accordingly, by counting the number of passing of the hole 17, the number of rotation of the guide roller 73, which is rotated by bearing the adhesive film 6, can be obtained, and movement of the adhesive film 6 can be calculated from the number of rotation.

The adhesive film 6 has such a property that a widthwise stripe is produced in the adhesive surface of the film 6 at the time of its stopping. Namely, as in the cases of cellophane tape and vinyl tape, the widthwise stripe is produced on the boundary between a part peeled from the roll for supplying the adhesive film 6 and a part which has not been peeled. When such a stripe comes within an image pick-up range for a camera, it affects the identification of particles of the powder or granular material, and obstructs data processing. By this reason, in this particle measurement device 1, the movement of the adhesive film 6 is detected by using the above-described sensor 16, to adjust the winding length of the adhesive film 6 so that the above-described stripe does not come within the image pick-up range and, at the same time, the adhesive film 6 can be used as effectively as possible.

Behind the adhesive film 6, for lighting the adhesive film 6, a circular fluorescent lamp 8 is provided being supported by a fluorescent lamp supporting portion 11. Further, behind the fluorescent lamp 8, is installed a CCD camera 7 (image pick-up means) for picking up a state of the powder or granular material adhering to the adhesive film 6. The fluorescent lamp supporting portion 11 is shielded for the light on its surface on the side of the CCD camera 7 so that the light of the fluorescent lamp 8 does not enter the CCD camera 7 directly. The pick-up data is transmitted to a control part (information processing unit) 12, and grain sizes etc. of all the powder or granular material adhering to the adhesive film 6 are measured.

Figure 3:
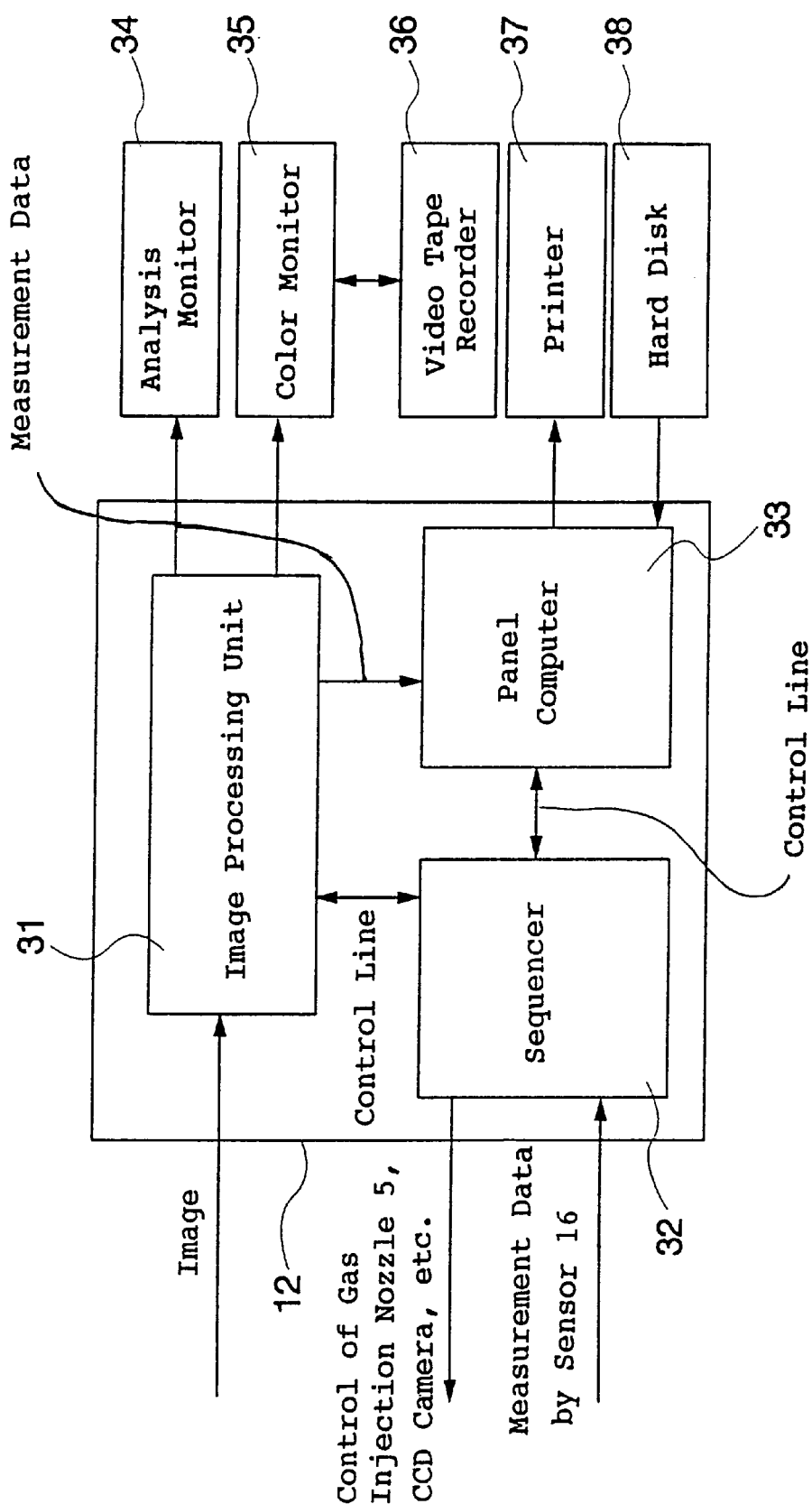
FIG. 3 is a block diagram showing construction of a control part of the particle measurement device of FIG. 1.

Here, the control part 12 is a part which performs image processing and control of the system as a whole, and, as shown in FIG. 3, comprises an image processing unit 31, a sequencer 32, and a panel computer 33. The image processing unit 31 processes a particle image from the CCD camera 7. The sequencer 32 obtains measurement data from the sensor 16, and controls the gas injection nozzle 5, the CCD camera 7, the air cylinder 15, the motor reel 72, and the like, to make them perform sampling operation and image pick-up operation. Further, the sequencer 32 also controls operation of the fluidized bed granulating apparatus 20. Further, the panel computer 33 receives data from the image processing unit 31 to perform various calculations, and controls the sequencer 32.

In addition, the control part 12 is equipped with an analysis monitor 34 for displaying a particle image undergone the image processing, so that a state of measurement of particle can be checked. Further, a color monitor 35, which displays images from the CCD camera 7, is also provided to the control part 12 so that colors, shapes and surface conditions of particles can be observed from the raw images of the particles. In addition, the control part 12 is equipped with a video tape recorder 36 for recording those images. Further, a printer 37 for printing out analysis results etc., and a hard disk as a storage means for storing various data such as the analysis results etc. are provided to the control part 12.

On the other hand, in the control part 12, measurement of particle diameter is performed as follows. Namely, first, in the image processing unit 31, analogue image sent from the CCD camera 7 is divided into 500×500 (=250,000) pixels, for example, and each pixel is digitized into a binary digit depending on its luminous intensity. This data is sent to the panel computer 33. Then, based on the received data, the panel computer 33 defines a projected area of a particle as an area of high-level pixels which continuously contact with one another, obtains a diameter of a supposed circle having the same area as the such-defined projected area, and gives this diameter as particle diameter data. From thus-obtained particle diameter data, grain size distribution, an average particle diameter, and the like are calculated. Further, from the projected particle image, a major diameter and a minor diameter are measured, and also a sphericity (ratio of the major diameter to the minor diameter) is calculated. With respect to these controls of the various devices by the control part 12 and calculations of the particle measurement through the image analysis by the control part 12, programs for the computer to execute these operations may be stored and handled in a medium.

Figure 4:
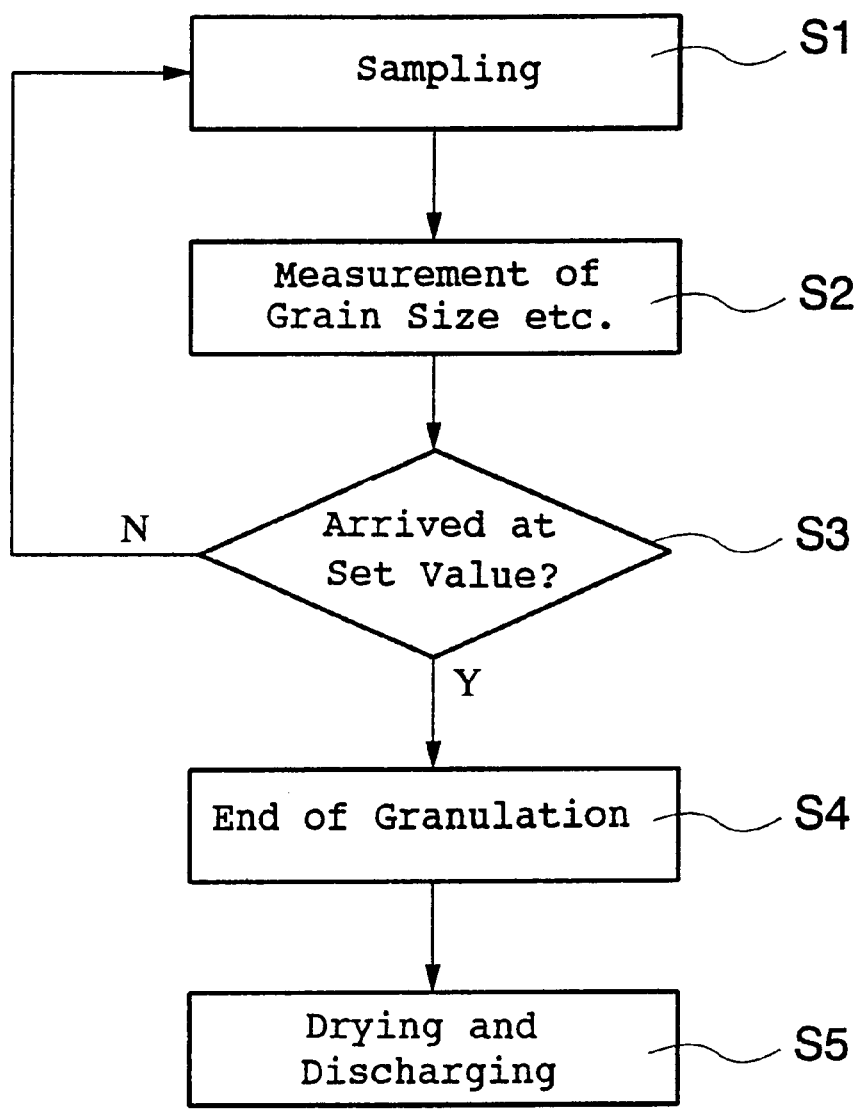
FIG. 4 is a flowchart showing an outline of operation in the case that granulation control of powder or granular material is performed using the particle measurement device of FIG. 1.

Next, operation of Embodiment 1 will be described. FIG. 4 is a flowchart showing an outline of the operation in the case that granulation control of powder or granular material is performed using the particle measurement device 1. Also, it is to be noted that programs may be stored and handled in a medium, so that, by these programs, the computer executes a procedure for measurement of powder or granular material, a procedure for deciding end of granulation, and granulation control, described below.

As shown in FIG. 4, in the particle measurement device 1 in question, first, sampling of the powder or granular material is performed (S1), and grain sizes etc. of the samples are measured (S2). Next, it is judged if the measured values arrive at preset values (S3). When they arrive at the preset values, the granulation is stopped (S4), and drying and discharging of the products are performed (S5). On the other hand, when they do not arrive at the preset values, the granulation operation is continued, and sampling is repeated at given time intervals (S1).

Here, first, in the particle measurement device 1 of Embodiment 1, gas for cleaning the drawing tube 3 is introduced always from the air inlet 4 into the drawing tube 3, so that air flow toward the granulating vessel is always produced within the drawing tube 3. On the other hand, when granulation is performed in the fluidized bed granulating apparatus, powder or granular material having various grain sizes etc. is fluidized to form a fluidized bed within the granulating vessel 2, and the inside of the granulating vessel 2 is at negative pressure slightly lower than the atmospheric pressure, although there exists large fluctuation of that negative pressure as described above.

Accordingly, in Embodiment 1, feeding quantity of the gas from the air inlet 4 and pressure difference from the inside of the granulating vessel 2 are set within suitable ranges, in order that pressure of the inside of the drawing tube 3 may not be lower than the pressure inside the granulating vessel 2 regardless of the pressure fluctuation inside the granulating vessel 2, and that high pressure gas injection from the gas injection nozzle 5 may cause a suitable number of powder or granular material to be captured by the adhesive film 6. By this, it is possible to suitably control the number of the powder or granular material adhering to the adhesive film 6, in the drawing tube 3 of Embodiment 1. In that case, supply pressure of the gas is set generally in the range of 0.5–5 kg/cm2, and preferably in the range of 0.1–3 kg/cm2. Preferably, the supply gas may be same as the gas existing inside the granulating vessel 2 although any gas may be used, and usually, air, i.e., atmospheric air is supplied.

Next, while the gas is introduced from the air inlet 4, high pressure gas is injected from the gas injection nozzle 5 so that the powder or granular material is introduced into the drawing tube 3. Here, the pressure of the gas injected from the gas injection nozzle 5, as well as the pressure of the gas introduced from the air inlet 4, is so adjusted to be a suitable value that the powder or granular material floating about the tip of the gas injection nozzle 5 arrives at the adhesive film 6. By this injection, all the powder or granular material floating in front of the gas injection nozzle collides against the adhesive film 6 through the drawing tube 3 and adheres to its adhesive surface. The injection of the high pressure gas may be suitably set, for example, in such a way that it is performed at given time intervals or at optionally predetermined times.

At the end of the gas injection, the CCD camera 7 takes a picture of the adhesive film 6 to which the powder or granular material adheres, with lighting of the fluorescent lamp 8, and the data is output into the control part 12. In the control part 12, for all the powder or granular material adhering to the adhesive film 6, grain sizes etc. are measured in the above-described manner. This means that the grain sizes etc. of the powder or granular material being fluidized at the time of granulation within the granulating vessel 2 are directly measured in real time.

The control of the granulation end point is performed by using data of grain size and sphericity, for example. In that case, the end point value or values are set for predetermined one or more factors, and a time point when actual measurement arrives at the set value is regarded as the granulation end point and the process in question is ended.

On the other hand, as for the time interval for the particle measurement, there may be set some modes such as a standard measurement mode, a high speed measurement mode, a programmed mode, and the like. In that case, in the standard measurement mode, for example, all the factors relating to particle diameter and sphericity are calculated, and the measurement interval can be selected in the range of 10–99 seconds. In the high speed mode, only data relating to particle diameter is measured, and the measurement interval is fixed to 5 seconds. Further, in the programmed mode, the measurement interval and frequency can be set freely and suitably.

After such measurement, the motor reel 72 is driven to draw out the adhesive film 6 by one pitch length. At that time, the adhesive film 6 with the adhered powder or granular material is peeled from the end surface 3c of the drawing tube 3 for the powder or granular material, and an unused portion of the film 6 is moved to a position opposed to the end surface 3c and tightly fixed to the end surface 3c, completing preparation of the next measurement. Control of these operations is performed also by the control part 12.

Thus, according to the particle measurement device 1 of Embodiment 1, the inside of the drawing tube 3 for powder or granular material is always kept clean by introducing gas at suitable pressure from the air inlet 4, and the number of the powder or granular material adhering to the adhesive film 6 can be controlled. The lower portion of the fluidized bed is crowded with the powder or granular material, and it is very difficult to identify individual particle by direct photographing of the crowded fluidized bed. However, according to the particle measurement device of the present invention, it is possible to measure the powder or granular material in the lower portion of the fluidized bed representing the population. Thus, irrespective of pressure fluctuation within the granulating vessel 2, accurate samples can be obtained always, and reliability of the measurement result is improved.

Figure 5:
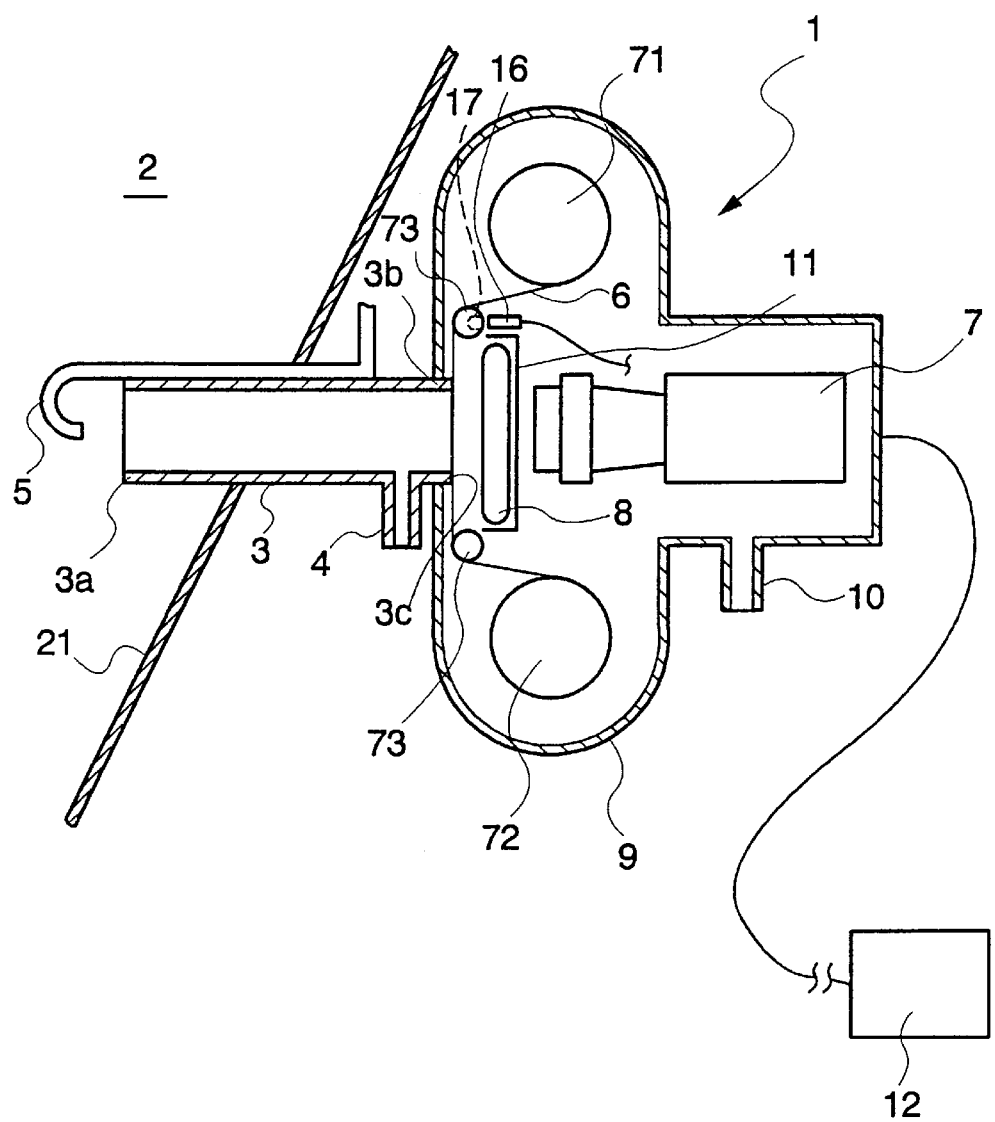
FIG. 5 is a partially sectional plan view showing construction of a particle measurement device for a powder or granular material processing apparatus, as a second embodiment of the present invention.

Next, there will be described a particle measurement device for a powder or granular material processing apparatus, as Embodiment 2 of the present invention. FIG. 5 is a plan view showing its construction. Also in FIG. 5, a part of the device is shown in section, as in FIG. 1.

As shown in FIG. 5, the particle measurement device 1 of Embodiment 2 has fundamental construction similar to the particle measurement device 1 of the previous Embodiment 1, except that a cover 9 covers a part on the outward side of the end portion 3b of the drawing tube 3. Namely, as seen from FIG. 5, the cover 9 contains the end portion 3b of the drawing tube 3, the adhesive film 6, the roll supporting portion 71, the motor reel 72, the guide rollers 73, 73, the fluorescent lamp 8, the fluorescent lamp supporting portion 11, and the CCD camera 7. The same reference numerals are given to parts common to Embodiment 1, and description of details of them is omitted in the following. Further, in the present embodiment, tensile force of the adhesive film is utilized for tightly fixing the film 6.

The cover 9 of Embodiment 2 is provided with an air feed port 10 communicated with the inside space of the cover 9 for cleaning the inside of the cover 9. The cover 9 is fitted to the drawing tube 3, being tightly coupled to the end portion 3b of the drawing tube 3, so as to realize sealed structure which is only opened at the air feed port 10 and the opening of the drawing tube 3. Accordingly, when the adhesive film 6 is tightly fixed to the end surface 3c, the inside of the cover 9 becomes a sealed space except for the opening of the air feed port 10.

In thus-constructed particle measurement device 1, similarly to Embodiment 1, the particle measurement is performed while cleaning the inside of the drawing tube 3 by introducing the gas through the air inlet 4. Operation at that time is similar to the case of Embodiment 1, and its detailed description is omitted. Then, after the particle measurement, the adhesive film 6 is moved by one pitch length for preparing the next measurement. At that time, the adhesive film 6 is peeled from the end surface 3c of the drawing tube 3 to be released from the tight condition before the movement, and, accordingly, there may be a gap between them and the powder or granular material may flow out through the gap.

Thus, in this Embodiment 2, at the time of the above-described movement, gas having slightly higher pressure than the inside of the granulating vessel 2 is introduced into the inside of the cover 9 through the air feed port 10.

Namely, at least when there exists the above-described gap, the gas is introduced so that the inside of the cover 9 is always at higher pressure than the inside of the drawing tube 3. Thus, in the gap between the end surface 3c of the drawing tube 3 and the adhesive film 6, is produced air flow toward the drawing tube 3 only, and the powder or granular material is prevented from flowing out from the drawing tube 3 to the cover 9. In that case, although the pressure of the gas introduced through the air feed port 10 varies depending on the model of the granulating apparatus, and the like, generally gas with pressure in the range of 0.05–5 kg/cm2, and preferably of 0.1–3 kg/cm2 is introduced.

Although it is sufficient that the gas is introduced through the air feed port 10 at least when the adhesive film 6 is moved, the inside of the cover 9 may always or suitably be kept at constant pressure slightly higher than the inside of the granulating vessel 2. In that case, when the gas is introduced, the adhesive film 6 is pressed against the end surface 3c of the drawing tube 3, so that the adhesive film 6 can be tightly in contact with the end surface 3c without employing other tight fixing means.

Thus, the present Embodiment 2 is constructed so that the cover 9 contains the part on the outward side of the end portion 3b of the drawing tube 3, including the fluorescent lamp 8 and the CCD camera 7. However, to prevent flow out of the powder or granular material through the gap, it is sufficient that, at minimum, the portion of the gap, i.e., the portion of the adhesive film 6 and the end surface 3c is covered by the cover 9. It, however, is convenient from the viewpoints of dust protection and of device construction that the cover 9 contains the CCD camera 7 etc. too.

As described above, according to the particle measurement device 1 of Embodiment 2, the cover 9 covers the portion between the end surface 3c of the drawing tube 3 and the adhesive film 6, and the inside of the cover 9 is set at slightly higher pressure than the inside of the granulating vessel 2, so that flow out of the powder or granular material through the gap therebetween can be prevented and the device can be kept in clean condition. In particular, the effect of preventing the flow out of the powder or granular material is large in the case that, in the neighborhood of the end portion 3a of the drawing tube, internal pressure of the fluidized bed on the side of the granulating vessel 2 becomes positive pressure.

Thus, in Embodiment 2, there has been described the case that the present invention is applied to the particle measurement device 1 provided with the air inlet 4. Of course, however, the above-described construction can be applied to an apparatus without the air inlet 4.

Figure 6:
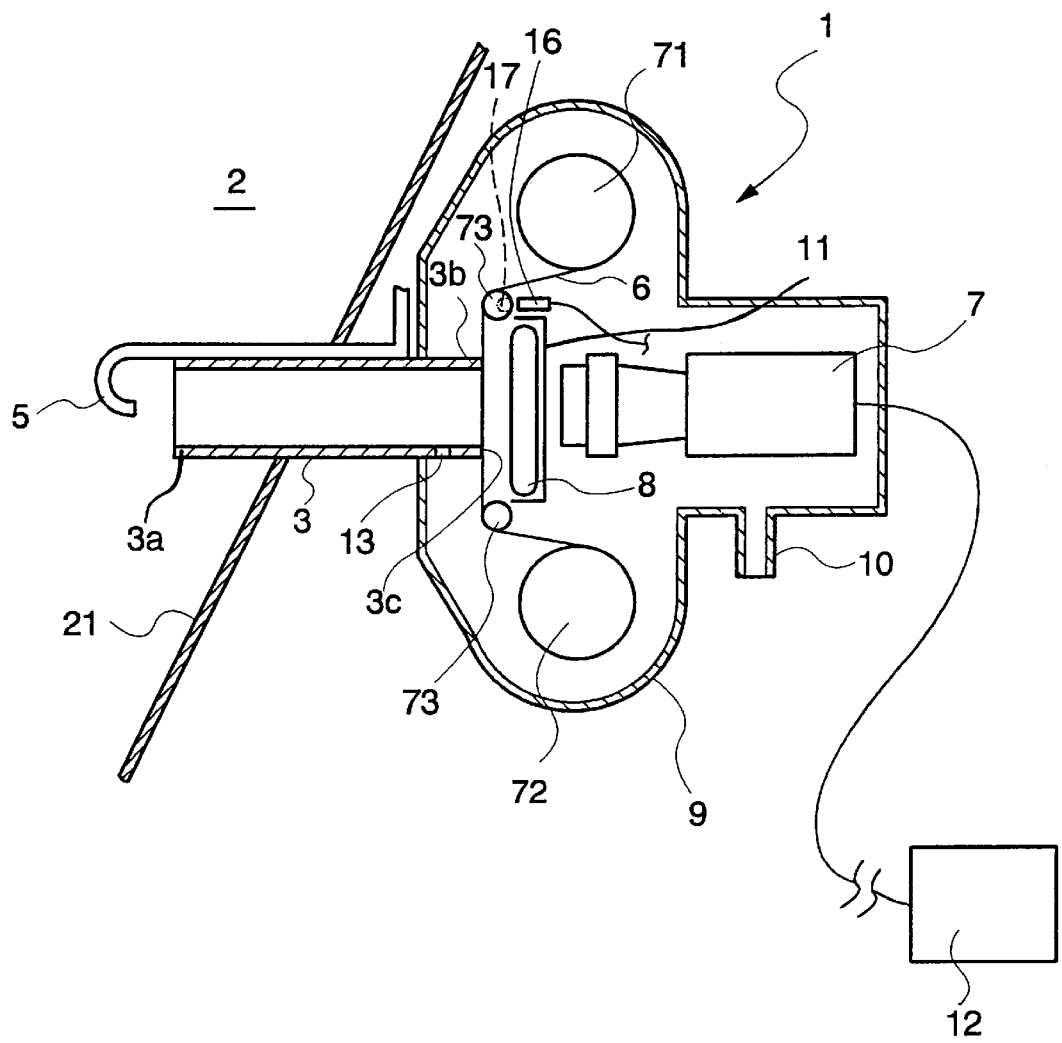
FIG. 6 is a partially sectional plan view showing construction of a particle measurement device for a powder or granular material processing apparatus, as a third embodiment of the present invention.

Next, there will be described a particle measurement device for a powder or granular processing apparatus, as Embodiment 3 of the present invention. FIG. 6 is a partially sectional plan view showing its construction.

As shown in FIG. 6, the particle measurement device 1 of Embodiment 3 has fundamental construction similar to the particle measurement device 1 of the previous Embodiment 2. Differently, however, from Embodiment 2, Embodiment 3 is provided with an air communicating port 13, instead of the air inlet 4, in the end portion 3b of the drawing tube 3 at its portion covered by the cover 9, and the part on the outer side from this air communicating port 13 is covered by the cover 9. Namely, as seen from FIG. 6, the cover 9 contains the end portion 3b of the drawing tube 3 and the air communicating port 13 provided therein, the adhesive film 6, the roll supporting portion 71, the motor reel 72, the guide rollers 73, 73, the fluorescent lamp 8, the fluorescent lamp support-ing portion 11, and the CCD camera 7. Also, like reference numerals will be given to like parts common to the previous Embodiments 1 and 2, and their detailed description will be omitted.

Here, the cover 9 of Embodiment 3 is provided with an air feed port 10 communicated with the inside space of the cover 9. Further, this air feed port 10 is communicated with the air communicating port 13 and the drawing tube 3 through the inside space of the cover 9. Similarly to Embodiment 2, the cover 9 is fitted to the end portion 3b of the drawing tube 3 in a tightly coupled state, and gives sealed construction except for the air communicating port 13 and the opening of the drawing tube 3. Thus, when the adhesive film 6 is tightly fixed to the end surface 3c of the drawing tube 3, the inside of the cover 9 becomes a sealed space with the air communicating port 13 and the air feed port 10 are communicated with each other.

In thus-constructed particle measurement device 1, gas at given pressure is always introduced through the air feed port 10 so that the pressure inside the cover 9 is slightly higher than the pressure inside the granulating vessel 2. In that case, feeding quantity of the gas introduced from the air feed port 10 and pressure difference from the inside of the granulating vessel 2 are set so that the pressure inside the cover 9 is slightly higher than the pressure inside the granulating vessel 2 regardless of pressure fluctuation within the granulating vessel 2, and so that the pressure inside the drawing tube 3 does not become lower than the pressure inside the granulating vessel 2 and the adhesive film 6 captures a suitable number of the powder or granular material by high pressure gas injection from the gas injection nozzle 5. Although such pressure at the air feed port 10 varies depending on a model of the granulating apparatus etc., it is generally in the range of 0.05–5 kg/cm2, and preferably in the range of 0.1–3 kg/cm2, for example.

Since the cover 9 is closed in the state that the air communicating port 13 and the air feed port 10 are communicated with each other, at the same time when gas is introduced through the air feed port 10, the gas is introduced into the drawing tube 3 through the air communicating port 13. Thus, the air communicating port 13 serves similarly to the air inlet 4 of Embodiment 1, and there are realized conditions similar to Embodiment 1. Namely, by this introduction of the gas, the powder or granular material remaining within the drawing tube 3 is returned into the granulating vessel 2, and the powder or granular material is prevented from flowing from the granulating vessel 2 into the drawing tube 3. Under such conditions, similarly to Embodiments 1 and 2, high pressure gas is injected from the gas injection nozzle 5 to perform the particle measurement. Operation at the time of the particle measurement is similar to the cases of Embodiments 1 and 2, and its detailed description is omitted here.

After the particle measurement, the adhesive film 6 is moved. In the present Embodiment 3, the gas at slightly higher pressure than the inside of the granulating vessel 2 is always introduced into the inside of the cover 9 through the air feed port 10, so that the inside of the cover 9 is always kept at higher pressure than the inside of the drawing tube 3. Namely, there are realized conditions similar to Embodiment 2. Thus, similarly to Embodiment 2, at the gap between the end surface 3c of the drawing tube 3 and the adhesive film 6, only air flow toward the drawing tube 3 is produced, and flow out of the powder or granular material from the drawing tube 3 toward the adhesive film 6 is prevented.

Thus, according to the particle measurement device 1 of Embodiment 3, the inside of the drawing tube 3 is always kept clean, and flow out of the powder or granular material through the gap between the end surface 3c of the drawing tube 3 and the adhesive film 6 is prevented.

Figure 7:
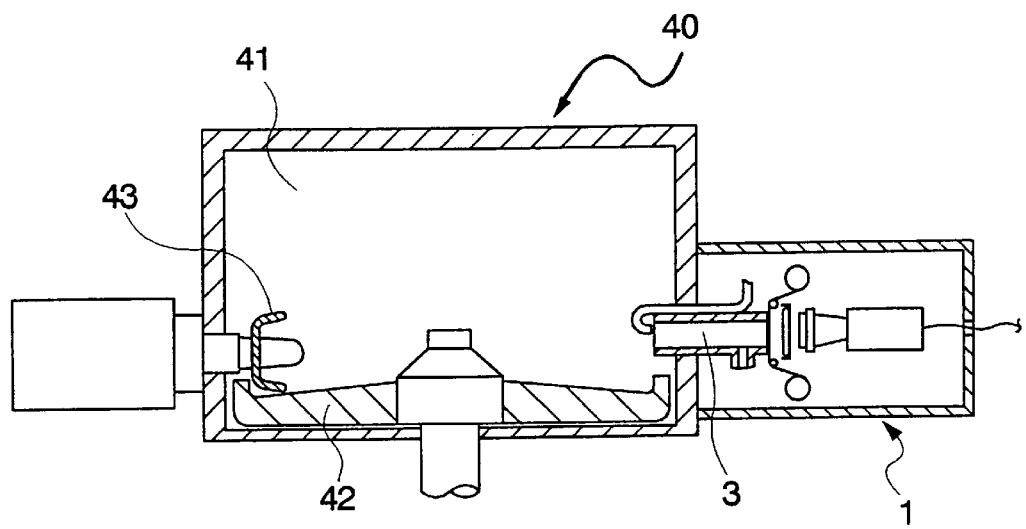
FIG. 7 is an explanatory view showing an example as a fourth embodiment of the present invention, in which the particle measurement device of FIG. 1 is attached to an agitation granulating apparatus.

Next, as Embodiment 4 of the present invention, there will be shown an example in which the particle measurement device of FIG. 1 is mounted in an agitation granulating apparatus. FIG. 7 is an explanatory view showing that example. The construction of the particle measurement device 1 is same as Embodiment, and its detailed description is omitted here.

Here, the agitation granulating apparatus 40 is so constructed that a bottom portion of a granulating vessel 41 serves as a fixed wall, an agitating blade 42 is provided therein, and a disintegrating blade 43 is provided in a side wall of the granulating vessel 41. By tumbling granulation with the agitating blade 42 and by disintegration granulation with the disintegrating blade 43, powder or granular material charged into the granulating vessel 41 is granulated.

As shown in FIG. 7, in the present Embodiment 4, the particle measurement device 1 is provided in a lower portion of the side wall of the granulating vessel 41. As described above, as the granulation process proceed, grain size etc. are suitably measured to control the granulation end point. In that case, conventionally in the agitation granulating apparatus 40, it is difficult to obtain an image of individual powder or granular material since particles are crowded within the granulating vessel 41. However, according to the particle measurement device 1 of the present invention, it is possible to accurately photograph only a part of the crowded particles, since the powder or granular material is sent into the drawing tube 3 by the high pressure gas from the gas injection nozzle 5, and the crowded particles are dispersed and fixed on the adhesive film 6 as individually identifiable particle. Namely, real-time measurement of grain size etc. is possible, and validation can be performed also in the agitation granulating apparatus, not only in the fluidized bed granulating apparatus.

Figure 8:
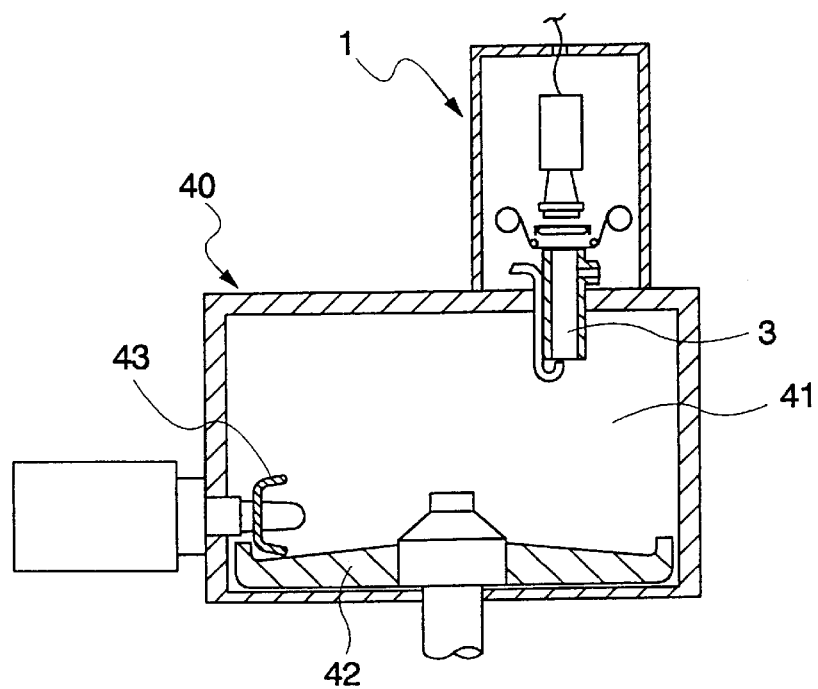
FIG. 8 is an explanatory view showing a variation of the example shown in FIG. 7.

As shown in FIG. 8, the particle measurement device 1 may be mounted in an upper portion of the granulating vessel 41. Although mounting position of the particle measurement device 1 is not limited to these examples, the construction shown in FIG. 7 is more advantageous than the one of FIG. 8 in adaptation for a larger machine. In Embodiment 4, there has been shown the example that the particle measurement device of FIG. 1 is mounted onto the agitation granulating apparatus. However, as the particle measurement device, one of FIG. 5 or 6 may be employed, of course.

Figure 9:
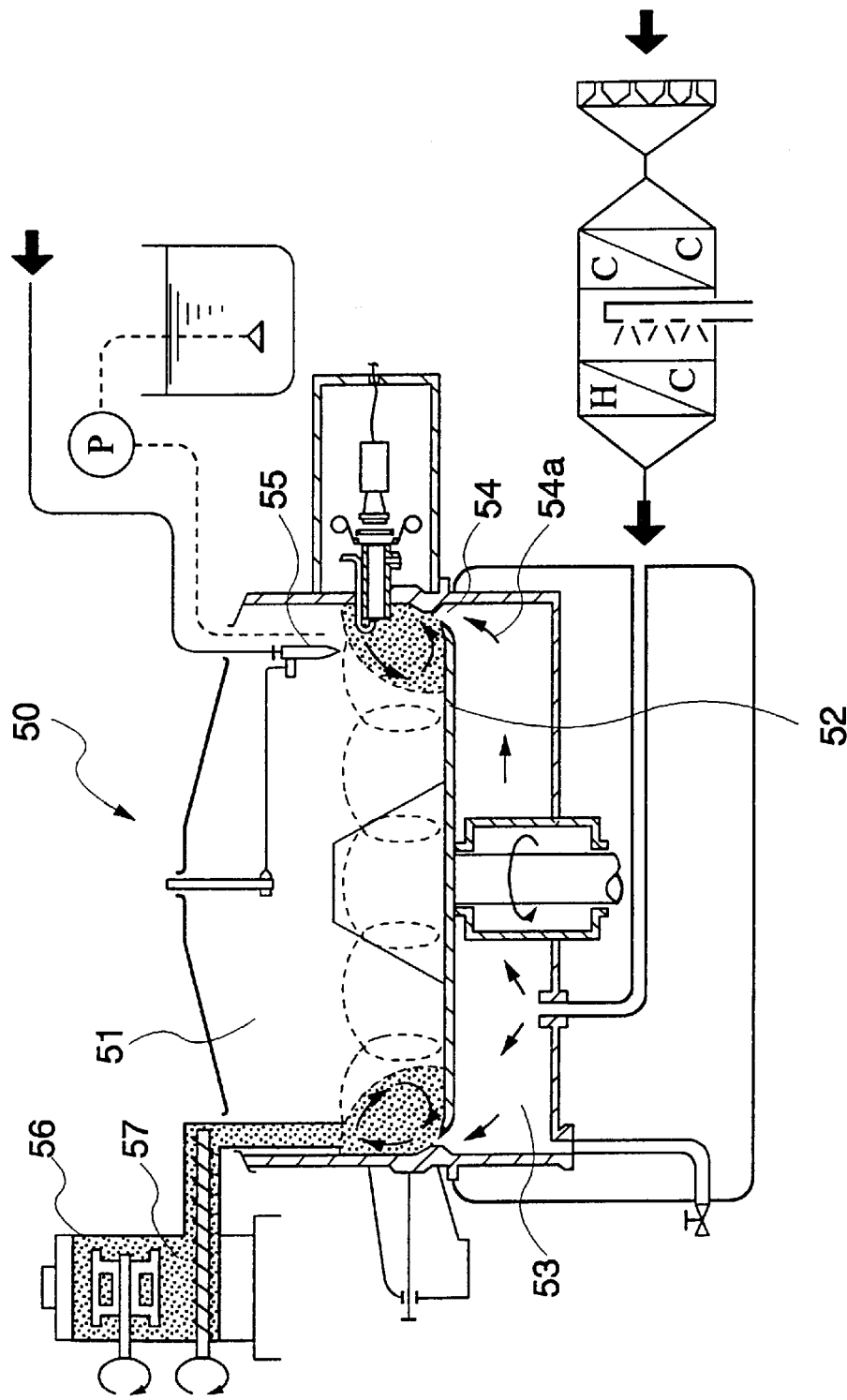
FIG. 9 is an explanatory view showing an example in which the particle measurement device of FIG. 1 is attached to a centrifugal tumbling granulating apparatus, as a fifth embodiment of the present invention.

Next, there will be shown Embodiment 5 of the present invention, in which the particle measurement device of FIG. 1 is mounted in a centrifugal tumbling granulating apparatus. FIG. 9 is an explanatory view showing this embodiment. The particle measurement device 1 has the same construction as described in Embodiment 1, and its detailed description is omitted here.

In this embodiment, the centrifugal tumbling granulating apparatus 50 has a rotating disk 52 provided within a granulating vessel 51, and by its rotation, granulation processing is performed on powder or granular material existing on the rotating disk 52. This centrifugal tumbling granulating apparatus 50 is a so-called centrifugal tumbling granulating and coating apparatus which performs granulation and coating by employing a centrifugal tumbling granulating method, and a slit 54 is opened between a side wall of a granulating vessel 51 of the apparatus and the rotating disk 52. Granulation processing is performed while slit air 44a is supplied from an air chamber 53 through the slit 54. Within the granulating vessel 51, liquid can be sprayed through a spray nozzle 55 and powder 57 can be spread from a powder spreading device 56.

As shown in FIG. 9, in the present Embodiment 5, the particle measurement device 1 is mounted in a central portion of the side wall of the granulating vessel 51 so that the end portion of the drawing tube 3 for drawing the powder or granular material is located slightly above the rotating disk 52. As described above, as the granulation process proceeds, grain size etc. are suitably measured to control granulation end point etc.

Conventionally in the centrifugal tumbling granulating apparatus, effective measurement has been impossible even employing a method of photographing in which the powder or granular material is brought into separated condition by air, since powder or granular material is very crowded in a lower portion of a particle bed where the powder or granular material representing the population exists. In other words, in the centrifugal tumbling apparatus, adaptation for validation has been impossible although improvement has been desired. However, according to the particle measurement device of the present invention, it is possible to measure grain size etc. in real time also in the centrifugal tumbling granulating apparatus, and validation is possible not only in the fluidized bed granulating apparatus but also in the centrifugal tumbling granulating apparatus. Further, grain size distribution of products becomes sharp, and yield of the product increases.

Similarly to Embodiment 4 shown in FIG. 8, in the present Embodiment 5, the particle measurement device may be installed in an upper portion of the apparatus. Further, in this Embodiment 5, there has been described the example that the particle measurement device of FIG. 1 is mounted in the centrifugal granulating apparatus. Of course, similarly to the case of Embodiment 4, as the particle measurement device, one shown in FIG. 5 or 6 may be employed.

Figure 10:
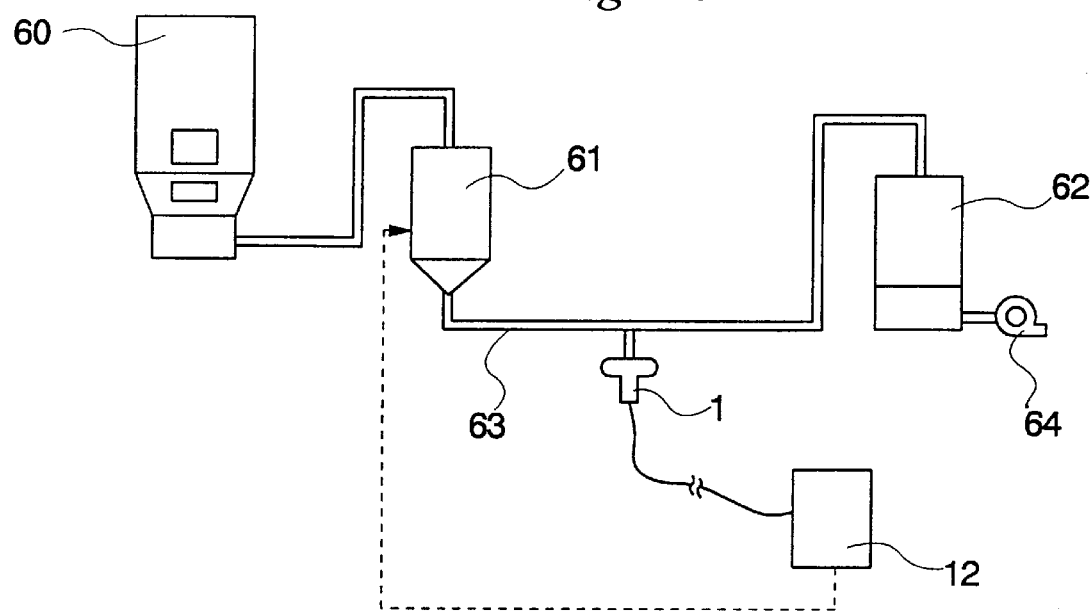
FIG. 10 is an explanatory view showing an example of a system in which feedback control is performed on a powder or granular material processing apparatus, by using the particle measurement device of FIG. 1, as a sixth embodiment of the present invention.

Next, there will be described Embodiment 6 of the present invention, in which the particle measurement device 1 according to the present invention is provided downstream from a powder or granular material processing apparatus which can perform continuous processing, and feedback control of the powder or granular material processing apparatus is performed. FIG. 10 is an explanatory view showing an outline of its system configuration.

As shown in FIG. 10, the system in question has the particle measurement device 1 provided downstream from a particle regulator 61 connected to the fluidized bed granulating apparatus 60. The particle measurement device 1 is installed in a powder or granular material transport pipe 63 provided between the particle regulator 61 and a recovery apparatus 62. The particle measurement device has the same construction as described in Embodiment 1, and its detailed description is omitted here. As the particle regulator 61 and the recovery apparatus 62, ordinary commercially-provided ones are employed. Further, out of the particle measurement devices 1 shown in FIGS. 1, 5 and 6, any one may be used, of course.

In the present system, the powder or granular material processed by the fluidized bed granulating apparatus 60 is sent to the particle regulator 61, and then transported to the recovery apparatus 62 through the powder or granular material transport pipe 63 by air flow caused by a blower 64. The particle measurement device 1, which is provided in the middle of the powder or granular material transport pipe 63, measures grain size etc. of the powder or granular material.

In that case, between the particle regulator 61 and the recovery apparatus 62, processing is performed continuously, and by suitably setting processing conditions such as rotation speed, air pressure, and the like, particle diameter of the powder or granular material can be varied. Thus, when the particle measurement device 1 is provided downstream from the particle regulator 61 as in the present system, and feedback control of the particle regulator 61 is performed based on the grain size etc. obtained in the particle measurement device 1, it is possible to perform processing which keeps the particle diameter within a given range.

Figure 11:
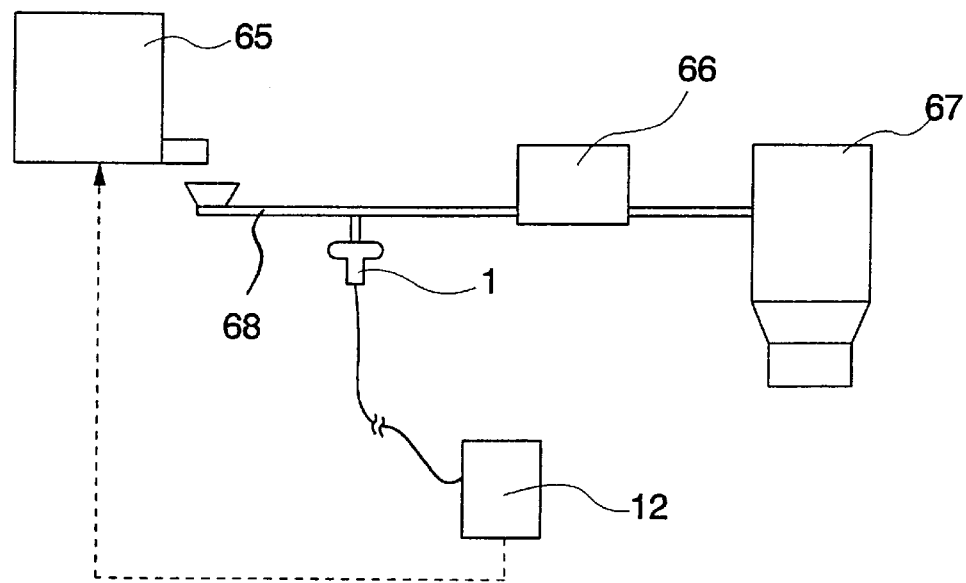
FIG. 11 is an explanatory view showing a variation of the example of FIG. 10.

On the other hand, as shown in FIG. 11, the particle measurement device of the present invention may be provided between an extrusion granulating apparatus 65 and a particle regulator 66. In that case, the powder or granular material is transported through a powder or granular material transport pipe 68 by negative pressure in a fluidized bed drying apparatus 67 provided downstream from the particle regulator 66 or by providing a blower which is not shown. Feedback control of the extrusion granulating apparatus 65 is performed based on the grain size etc. obtained by the particle measurement device 1. Further, in these examples, feedback control may be carried out, also by providing the particle measurement device 1 to the recovery apparatus 62 or to the particle regulator 66.

Thus, as described above, the particle measurement device 1 of the present invention can be applied to feedback control of not only an apparatus which performs batch type processing such as an agitation granulating apparatus, a fluidized bed granulating apparatus, or the like, but also an apparatus which performs continuous processing and can vary particle diameter by setting conditions such as a particle regulator, an extrusion granulating apparatus, a crusher, or the like. Further, the particle measurement device 1 of the present invention can be installed not only between powder or granular material processing apparatuses but also between a powder or granular material processing apparatus and a powder or granular material containing means such as a containing vessel. Further, the particle measurement device 1 can be installed between powder or granular material containing means, and, for example, the present particle measurement device may be installed between powder or granular containing vessels provided to respective powder or granular material processing apparatuses which perform batch processing.

Further, it goes without saying that the above-described feedback control can be applied not only for control of a preceding-stage apparatus by measuring end products, but also for control of production process of intermediate product such as one which is to be tabletted after granulation, for example. Further, the powder or granular material processing apparatus to which the present particle measurement device is mounted is not limited to the above examples, and the present device can be mounted to various apparatuses such as a crusher etc. Further, in the case that the particle measurement device is installed between powder or granular material processing apparatuses, combination of these apparatuses is not limited to the above-described examples, and various variations are possible.

Next, there will be described experimental results of measuring grain size etc. by using the particle measurement device of the present invention actually.

In this experiment, the above-described particle measurement device 1 was employed in Spir-A-Flow Model 5 (trade name), a combined-type fluidized bed granulating apparatus made by Freund Industrial Co., Ltd. so as to control granulation end point. In that case, a rotor and an agitator were mounted to the above Spir-A-Flow Model 5 to perform granulation processing in the combined form of the fluidized bed granulating method, the agitation granulating method, and the centrifugal tumbling granulating method.

In this experiment, 3500 g of 200 M (mesh) lactose, 1500 g of corn starch, and 250 g of HPC-L (hydroxypropyl cellulose) made by Nippon Soda Co., Ltd. were used, and granulation was performed while water was sprayed. As for the operating conditions of the apparatus, supply air temperature was 80° C., rotation speed of the rotor was 300 rpm, rotation speed of the agitator was 450 rpm, and speed of sprayed liquid was 100 ml/min.

Figure 12:
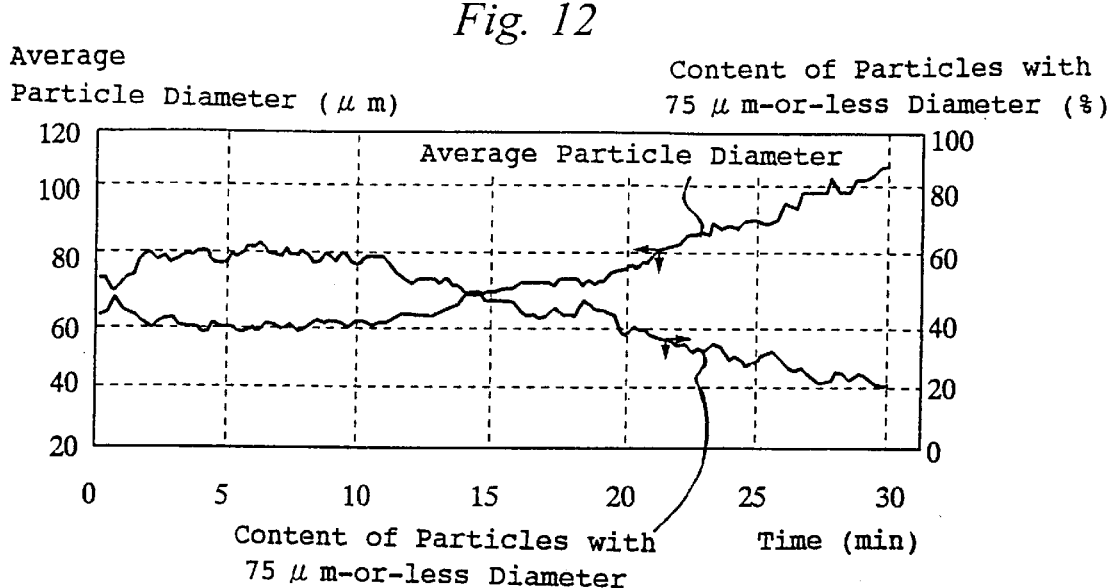
FIG. 12 is a graph showing time variations of average particle diameter and content of particles with 75 μm-or-less diameter in the batch No. 1.

Sampling by the particle measurement device 1 was performed every 15 seconds, to measure an average particle diameter and grain size distribution. Each of these values was calculated based on the numbers. In that case, as for referential batch No. 1, spraying was stopped at 30 minutes after the start of granulation and data was obtained. FIG. 12 is a graph showing time variations of average particle diameter and content of particles with 75 $\mu$m-or-less diameter in that case, showing that average particle diameter increased with time and the ratio of fine powder was decreased. Table 1 shows the measurement result just before the stopping of spraying.

TABLE 1

Batch No. 1 Measurement Data by Particle Measurement Device

| Time<br>No. 1 (minute.second) | 29.00 | 29.15 | 29.30 | 29.45 | 30.00 |
|---|---|---|---|---|---|
| Average Particle Diameter ($\mu$m) | 104 | 106 | 108 | 109 | 109 |
| Content of Particle with 75 $\mu$m-or-less Diameter (%) | 22.6 | 21.7 | 19.8 | 19.6 | 19.1 |

Based on these values, control of granulation end point was performed noting two conditions: (1) 108 $\mu$m or more was repeated 3 times continually as the average particle diameter; and (2) 75 $\mu$m or less was repeated 3 times continually as the content of particles with 75 $\mu$m-or-less diameter is 20% or less.

Measurement results for batches Nos. 2 and 3 are shown in Table 2.

TABLE 2

Batch No. 1 Measurement Data by Particle Measurement Device

| Time<br>No. 2 (minute.second) | 25.30 | 25.45 | 26.00 | 26.15 | 26.30 |
|---|---|---|---|---|---|
| Average Particle Diameter ($\mu$m) | 105 | 107 | 110 | 111 | 111 |
| Content of Particle with 75 $\mu$m-or-less Diameter (%) | 21.1 | 20.1 | 18.5 | 18.3 | 17.7 |
| Time<br>No. 3 (minute.second) | 27.45 | 28.00 | 28.15 | 28.30 | 28.45 |
| Average Particle Diameter ($\mu$m) | 101 | 104 | 107 | 109 | 109 |
| Content of Particle with 75 $\mu$m-or-less Diameter (%) | 22.5 | 21.1 | 19.6 | 18.6 | 18.8 |

In each batch including No. 1, there was good correlation between the average particle diameter and the content of particles with 75 $\mu$m-or-less diameter. Accordingly, which ever of the end point control conditions (1) and (2) was used, spraying could be stopped nearly at the same time.

Figure 13:
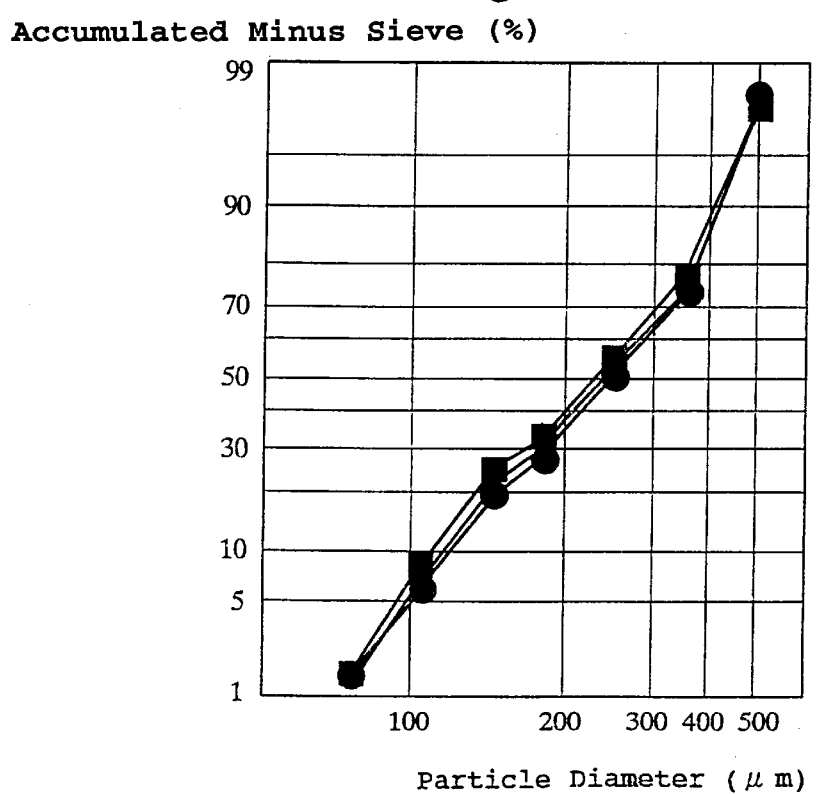
FIG. 13 is a graph showing grain size distributions for batches Nos. 1–3 obtained by a low tap sieve shaker.

FIG. 13 shows grain size distributions for the batch Nos. 1–3 obtained by a low tap sieve shaker. The grain size distributions of the granulated products generally coincide with one another. Thus, it was confirmed that the control of the granulation end point using the particle measurement device of the present invention was appropriate.

Figure 14:
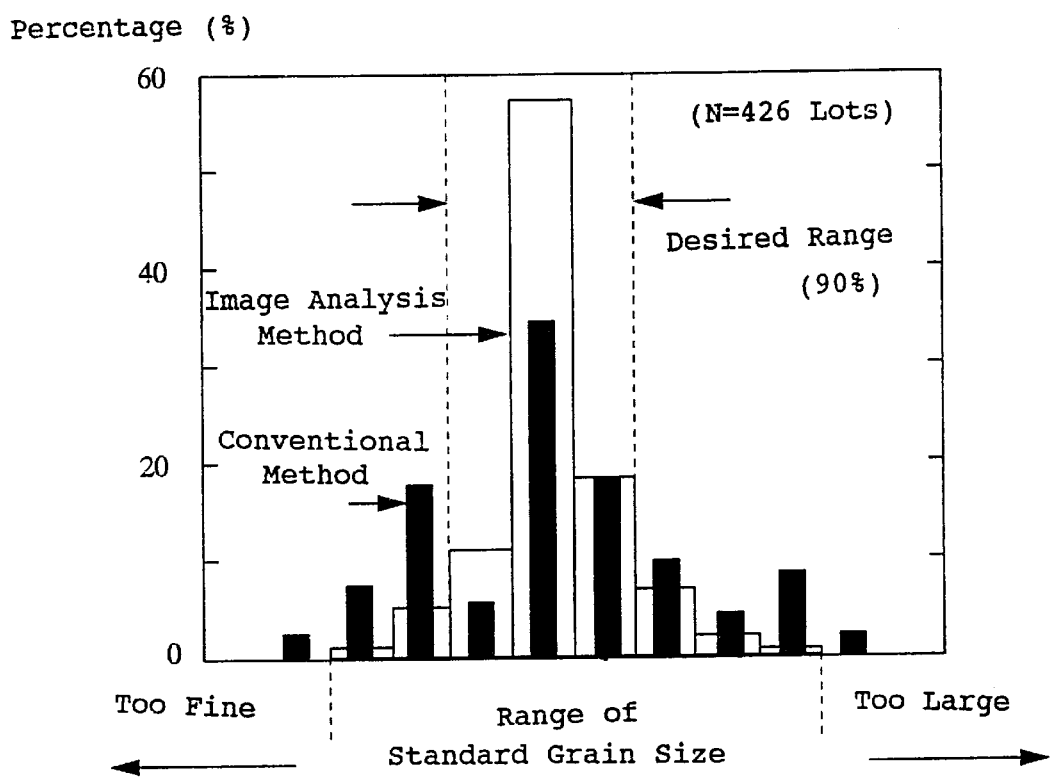
FIG. 14 is a graph showing comparison between granulated products obtained in the case that control of granulation end point is performed using the particle measurement device of the present invention and granulated products obtained in the case that control of granulation end point is performed by the conventional method.

FIG. 14 shows comparison between granulated products obtained in the case that control of the granulation end point is performed using the image analysis method employing the particle measurement device 1 of the present invention and granulated products obtained in the case that control of the granulation end point is performed using 16 mesh sieve as in the conventional method and judging from remaining particles on the sieve. As clearly seen from FIG. 14, a standard range of desirable grain size contains 90% of the products obtained by the particle measurement device of the present invention which employs the image analysis method. And it was found that a non-standard lot was not produced. Thus, in comparison with the conventional method, more precise control can be performed by using the particle measurement device of the present invention employing the image analysis method.

Hereinabove, the invention made by the present inventor has been described based on its embodiments. However, the present invention, of course, is not limited to the above-described embodiments, and can be changed variously without departing from the scope of the invention.

For example, in the above-described Embodiments 1–6, the control part has been employed as the information processing means. However, means for processing information is not limited to this, and the data analysis may be carried out using a personal computer etc. Further, the shape of the drawing tube for drawing out the powder or granular material is not limited to the one of the cylindrical shape, and a conical one may be employed. Further, as the image pick-up means, one other than a CCD camera, for example a still camera, may be used.

In the above-described Embodiments 1–6, the control of the granulation end point is performed by photographing particles with the particle measurement device. In addition to this, water content may be controlled by measuring water content in particle surfaces with an infrared moisture meter.

In the above, the invention made by the present inventor has been described for the case that it is applied to the fluidized bed granulating apparatus as its field of utilization. However, the present invention is not limited to this, and may be applied to measurement of grain size etc. of powder or granular material in a powder or granular material drying apparatus, a crusher, a coating apparatus, and the like.

The effect obtained by the representative of the inventions disclosed herein will be described as follows.

Namely, by providing the air inlet to the drawing tube of the particle measurement device for a powder or granular material processing apparatus, the inside of the drawing tube can be always kept clean, and it is possible to control the number of powder or granular material adhering to the adhesive film at the time of the particle measurement. Accordingly, without being affected by pressure fluctuation within the processing vessel, accurate samples can be obtained always, and reliability of the measurement result is improved.

Further, since at least portion between the end surface of the drawing tube and the adhesive film is covered by the cover, and its inside is made to be at slightly higher pressure than the inside of the processing vessel, it is possible to prevent flow out of the powder or granular material through the gap between them. Accordingly, contamination of the apparatus by flow out of the powder or granular material can be prevented, and the apparatus is kept in a clean condition.

We claim:

1. A particle measurement device for a powder or granular material processing apparatus, comprising:

a drawing tube for drawing out powder or granular material, with one end portion being arranged in an inside of a container forming a part of the powder or granular material processing apparatus and containing the powder or granular material to be measured, and with the other end portion being communicated with said one end portion and positioned outside of the container;

a gas injection nozzle for injecting high pressure gas from the inside of the container into the drawing tube, so as to introduce the powder or granular material within the container into the drawing tube;

an adhesive film with an adhesive surface being arranged opposed to an opening of an end surface of said drawing tube on the side of the outside of the container, so as to capture, with said adhesive surface, the powder or granular material which has passed the drawing tube;

an image pick-up means for photographing the powder or granular material captured by the adhesive surface of the adhesive film;

an information processing means for processing image information of the powder or granular material obtained by said image pick-up means; and a gas inlet communicated with the drawing tube in a neighborhood of the end portion of the drawing tube on the outside of the container for introducing into the drawing tube through said gas inlet a gas having a higher pressure than that existing inside of the container.

2. The particle measurement device for a powder or granular material processing apparatus according to claim 1, wherein:

said powder or granular material processing apparatus is a fluidized bed granulating apparatus.

3. The particle measurement device for a powder or granular material processing apparatus according to claim 1, wherein:

said powder or granular material processing apparatus is a fluidized bed coating apparatus.

4. The particle measurement device for a powder or granular material processing apparatus according to claim 1, wherein:

said powder or granular material processing apparatus is a fluidized bed drying apparatus.

5. The particle measurement device for a powder or granular material processing apparatus according to claim 1, wherein:

said powder or granular material processing apparatus is an agitation granulating apparatus.

6. The particle measurement device for a powder or granular material processing apparatus according to claim 1, wherein:

said powder or granular material processing apparatus is a centrifugal tumbling granulating apparatus.

7. The particle measurement device for a powder or granular material processing apparatus according to claim 1, wherein:

said powder or granular material processing apparatus is a centrifugal tumbling coating apparatus.

8. The particle measurement device for a powder or granular material processing apparatus according to claim 1, wherein:

said processing apparatus includes a processing vessel in which said powder or granular material can be processed continuously, said container in which said particle measurement device is installed is located downstream from said processing vessel and the conditions of the powder or granular material processing carried out in the processing vessel are controlled based on measurements made by the particle measurement device.

9. The particle measurement device for a powder or granular material processing apparatus according to claim 8, wherein:

said container in which said particle measurement device is installed is a transport pipe for transporting the material from the processing vessel.

10. A method of controlling a powder or granular material processing apparatus, using the particle measurement device according to claim 1, wherein:

said processing apparatus includes a processing vessel in which said powder or granular material is processed continuously, said particle measurement device is installed downstream from the processing vessel; and the conditions of the processing of the powder or granular material in the processing vessel are controlled based on measurements made by the particle measurement device.

11. The method of controlling a powder or granular material processing apparatus according to claim 10, wherein:

the container in which said particle measurement device is installed is a transport pipe for transporting the powder or granular material away from the processing vessel.

12. A particle measurement device for a powder or granular material processing apparatus, comprising:

a drawing tube for drawing out powder or granular material, with one end portion being arranged in an inside of a container forming part of the powder or granular material processing apparatus and containing the powder or granular material to be measured, and with the other end portion being communicated with said one end portion and positioned outside of the container;

a gas injection nozzle for injecting high pressure gas from the inside of the container into the drawing tube, so as to introduce the powder or granular material within the container into the drawing tube;

an adhesive film with an adhesive surface being arranged opposed to an opening of an end surface of said drawing tube on the side of the outside of the container, so as to capture, with said adhesive surface, the powder or granular material which has passed the drawing tube;

an image pick-up means for photographing the powder or granular material captured by the adhesive surface of the adhesive film;

an information processing means for processing image information of the powder or granular material obtained by said image pick-up means;

a gas communicating port communicated with said drawing tube in a neighborhood of the end portion of said drawing tube; and said gas communicating port being housed within a box together with said adhesive film and the end portion of the drawing tube opposed to the adhesive film;

said box having a gas feed port for introducing a gas having a higher pressure than that existing inside of the container into the box through said gas feed port.

13. A method of particle measurement for a powder or granular material processing apparatus using the particle measurement device of claim 12, comprising steps of:

injecting high pressure gas from said gas injection nozzle so as to introduce powder or granular material inside said container into said drawing tube;

capturing powder or granular material which has passed into the drawing tube with the adhesive surface of said adhesive film; and photographing the powder or granular material captured by the adhesive film to obtain image information, and, based on the obtained image information, obtaining information on the powder or granular material within the container;

constantly introducing gas having a higher pressure than that existing inside of the container into said box through said gas feed port so as to keep the inside of the box at higher pressure than the inside of the container; and performing said particle measurement while a gas having higher pressure than that existing inside of the container is constantly introduced into the drawing tube through said gas feed port.

14. A method of particle measurement for a powder or granular material processing apparatus, using the particle measurement device of claim 1, comprising steps of:

injecting high pressure gas from said gas injection nozzle so as to introduce powder or granular material inside said container into said drawing tube;

capturing the powder or granular material which has passed the drawing tube with the adhesive surface of said adhesive film;

photographing the powder or granular material captured by the adhesive film to obtain image information, and, based on the obtained image information, obtaining information on the powder or granular material within the container; and performing said particle measurement while gas having higher pressure than the inside of the container is constantly introduced into said drawing tube through said gas inlet.

15. The method of particle measurement for the powder or granular material processing apparatus according to claim 14, wherein:

said powder or granular material processing apparatus is a centrifugal tumbling granulating apparatus.

16. The method of particle measurement for the powder or granular material processing apparatus according to claim 14, wherein:

said powder or granular material processing apparatus is a centrifugal tumbling coating apparatus.

17. The method of particle measurement for the powder or granular material processing apparatus according to claim 14, wherein:

said powder or granular material processing apparatus is a fluidized bed granulating apparatus.

18. The method of particle measurement for the powder or granular material processing apparatus according to claim 14, wherein:

said powder or granular material processing apparatus is a fluidized bed coating apparatus.

19. The method of particle measurement for the powder or granular material processing apparatus according to claim 14, wherein:

said powder or granular material processing apparatus is a fluidized bed drying apparatus.

20. The method of particle measurement for the powder or granular material processing apparatus according to claim 14, wherein:

said powder or granular material processing apparatus is an agitation granulating apparatus.

* * * * *